(12) United States Patent
Lin et al.

(10) Patent No.: US 11,690,540 B2
(45) Date of Patent: Jul. 4, 2023

(54) SYSTEMS, METHODS, AND APPARATUS FOR DIFFERENTIAL PHASE CONTRAST MICROSCOPY BY TRANSOBJECTIVE DIFFERENTIAL EPI-DETECTION OF FORWARD SCATTERED LIGHT

(71) Applicant: The General Hospital Corporation, Boston, MA (US)

(72) Inventors: Charles P. Lin, Arlington, MA (US); Hari Prasad Paudel, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 603 days.

(21) Appl. No.: 16/773,438

(22) Filed: Jan. 27, 2020

(65) Prior Publication Data
US 2020/0237272 A1   Jul. 30, 2020

Related U.S. Application Data

(60) Provisional application No. 62/892,621, filed on Aug. 28, 2019, provisional application No. 62/796,703, filed on Jan. 25, 2019.

(51) Int. Cl.
*A61B 5/145*   (2006.01)
*G02B 21/14*   (2006.01)
(Continued)

(52) U.S. Cl.
CPC ........ *A61B 5/14535* (2013.01); *A61B 5/0068* (2013.01); *A61B 5/1455* (2013.01);
(Continued)

(58) Field of Classification Search
CPC . A61B 5/14535; A61B 5/0068; A61B 5/1455; A61B 2562/0233; G01N 15/1436;
(Continued)

(56) References Cited

U.S. PATENT DOCUMENTS 5,598,842 A   2/1997   Ishihara
6,538,730 B2   3/2003   Vaez-Iravani
(Continued)

FOREIGN PATENT DOCUMENTS

WO   1996037767 A1   11/1996

OTHER PUBLICATIONS

Hari P. Paudel, Clemens Alt, Judith Runnels, and Charles P. Lin, "Pupil plane differential detection microscopy," Opt. Lett. 43, 4410-4412 (2018) (Year: 2018).*

(Continued)

*Primary Examiner* — Dominic J Bologna
(74) *Attorney, Agent, or Firm* — Quarles & Brady LLP

(57) ABSTRACT

Systems, methods, and apparatus for differential phase contrast microscopy by transobjective differential epi-detection of forward scattered light are provided. In some embodiments, a microscope objective comprises: a housing with mounting threads at a second end; optical components defining an optical axis, comprising: an objective lens mounted at a first end, configured to collect light from a sample placed in a field of view, the plurality of optical components create a pupil plane at a first distance along the optical axis at which rays having the same angle of incidence on the objective lens converge at the same radial distance from the optical axis; a photodetector within the housing offset from the optical axis at a second distance along the optical axis; and another photodetector within the housing at second distance along the optical axis and offset from the optical axis in the opposite direction from the first photodetector.

23 Claims, 14 Drawing Sheets
(6 of 14 Drawing Sheet(s) Filed in Color)

(51) Int. Cl.
- G02B 21/00 (2006.01)
- A61B 5/1455 (2006.01)
- G01N 15/14 (2006.01)
- A61B 5/00 (2006.01)
- G02B 21/08 (2006.01)
- G02B 26/12 (2006.01)
- G02B 21/36 (2006.01)
- G01N 15/10 (2006.01)
- G01N 15/00 (2006.01)

(52) U.S. Cl.
CPC ..... *G01N 15/1436* (2013.01); *G01N 15/1468* (2013.01); *G02B 21/002* (2013.01); *G02B 21/008* (2013.01); *G02B 21/0048* (2013.01); *G02B 21/0056* (2013.01); *G02B 21/0068* (2013.01); *G02B 21/086* (2013.01); *G02B 21/14* (2013.01); *G02B 21/365* (2013.01); *G02B 26/12* (2013.01); *A61B 2562/0233* (2013.01); *G01N 2015/0065* (2013.01); *G01N 2015/1006* (2013.01); *G01N 2015/144* (2013.01)

(58) Field of Classification Search
CPC ....... G01N 15/1468; G01N 2015/0065; G01N 2015/1006; G01N 2015/144; G02B 21/002; G02B 21/0048; G02B 21/0056; G02B 21/0068; G02B 21/008; G02B 21/086; G02B 21/14; G02B 21/365; G02B 26/12

See application file for complete search history.

(56) References Cited

U.S. PATENT DOCUMENTS

| | | | |
|---|---|---|---|
| 7,264,794 | B2 | 9/2007 | Georgakoudi |
| 7,602,501 | B2 | 10/2009 | Ralston |
| 7,745,155 | B2 | 6/2010 | Lin |
| 8,108,031 | B2 | 1/2012 | Georgakoudi |
| 8,184,298 | B2 | 5/2012 | Popescu |
| 9,564,291 | B1 * | 2/2017 | Own ................. H01J 37/222 |
| 9,772,282 | B2 | 9/2017 | Tucker-Schwartz |
| 10,156,479 | B2 * | 12/2018 | Liu ................... G01N 15/1429 |
| 10,429,629 | B1 | 10/2019 | Brundage |
| 2006/0134003 | A1 | 6/2006 | Georgakoudi |
| 2015/0087902 | A1 | 3/2015 | Mertz |
| 2015/0285685 | A1 | 10/2015 | Wax |
| 2017/0363582 | A1 | 12/2017 | Mertz |

OTHER PUBLICATIONS

Hari P. Paudel, Yookyung Jung, Anthony Raphael, Clemens Alt, Juwell Wu, Judith Runnels, Charles P. Lin, "In vivo flow cytometry for blood cell analysis using differential epi-detection of forward scattered light," Proc. SPIE 10497, Imaging, Manipulation, and Analysis of Biomolecules, Cells, Tissue (Year: 2018).*

Alt, C. et al, "Retinal flow cytometer," Optics letters, vol. 32, No. 23, pp. 3450-3452, 2007.

Ba, C., et al. "Dual-modality endomicroscopy with co-registered fluorescence and phase contrast." Biomedical optics express 7.9 (2016): 3403-3411.

Bourquard, A. et al, "Analysis of White Blood Cell Dynamics in Nailfold Capillaries," in Conj Proc IEEE Eng Med Biol Soc, 2015.

Chen, C.L. et al, "Deep Learning in Label-free Cell Classification," Scientific Reports, vol. 6, p. 21471, 2016.

Chen, N. et al, "Recent Advances in Optical Microscopy Methods for Subcellular Imaging of Thick Biological Tissues," Critical Reviews in Biomedical Engineering, vol. 41, No. 4-5, pp. 393-403, 2015.

Chui, Typ, et al. "The use of forward scatter to improve retinal vascular imaging with an adaptive optics scanning laser ophthalmoscope." Biomedical optics express 3.10 (2012): 2537-2549.

Ford, T.N. et al, "Phase-gradient microscopy in thick tissue with oblique back-illumination," Nature Methods, vol. 9, No. 12, pp. 1195-1197, 2012.

Golan, L., et al. "High-speed interferometric spectrally encoded flow cytometry." Optics letters 37.24 (2012): 5154-5156.

Golan, L., et al. "Noninvasive imaging of flowing blood cells using label-free spectrally encoded flow cytometry," Biomedical Optics Express, vol. 3, No. 6, p. 1455, 2012.

Huang, D., et al. "Optical coherence tomography." science 254. 5035 (1991): 1178-1181.

Lee, H. et al, "In vivo imaging flow cytometer," Optics express, vol. 14, No. 17, pp. 7789-7800, 2006.

Mertz, J., et al. "Phase-gradient contrast in thick tissue with a scanning microscope." Biomedical optics express 5.2 (2014): 407-416.

Morgan S., "Can new optical techniques for in vivo imaging and flow cytometry of the microcirculation benefit sickle cell disease research?," Cytometry, vol. 79, No. 10, p. 766-774, 2011.

Nomarski G., "Micro Interfermotere defferentiel a ondes polarisees," J. Phys Radium 16, S9-S13 (1955).

Novak, J. et al, "In vivo flow cytometer for real-time detection and quantification of circulating cells," Optics letters, vol. 4, pp. 77-79, 2004.

Ntziachristos V., "Going deeper than microscopy: the optical imaging frontier in biology," Nature Methods, vol. 7, No. 8, 2010.

Paudel, H. P., et al. "In vivo flow cytometry for blood cell analysis using differential epi-detection of forward scattered light." In SPIE Proc of Imaging, Manipulation and Analysis of Biomolecules, San Francisco 2018.

Scoles, D., et al. "In vivo imaging of human cone photoreceptor inner segments." Investigative ophthalmology & visual science 55.7 (2014): 4244-4251.

Tsang, Tyf. "Optical third-harmonic generation at interfaces." Physical Review A 52.5 (1995): 4116.

Watt, F.M. et al. "Cell-extracellular matrix interactions in normal and diseased skin." Cold Spring Harbor Perspectives in Biology 3.4 (2011): a005124.

Webb R.H., "Theoretical basis of confocal microscopy," Methods Enzymol, vol. 307, p. 3-20, 1999.

Winer, M.M. et al, "In vivo noninvasive microscopy of human leucocytes," Scientific Reports, vol. 7, No. 1, p. 130 31, 2017.

Wu, C.-H. et al, "Imaging Cytometry of Human Leukocytes with Third Harmonic Generation Microscopy," Scientific Reports, vol. 6, No. 1, p. 37210, 2016.

Xu C. et al, "Recent advances in fiber lasers for nonlinear microscopy," Nature Photonics, vol. 7, pp. 875-882, 2013.

Yun S.H., "Light in diagnosis, therapy and surgery," Nat. Bio. Eng., vol. 1, No. 8, 2017.

Zhang, C. et al, "Stimulated Raman scattering flow cytometry for label-free single-particle analysis," Optica, vol. 4, No. 1, pp. 103-109, 2017.

* cited by examiner

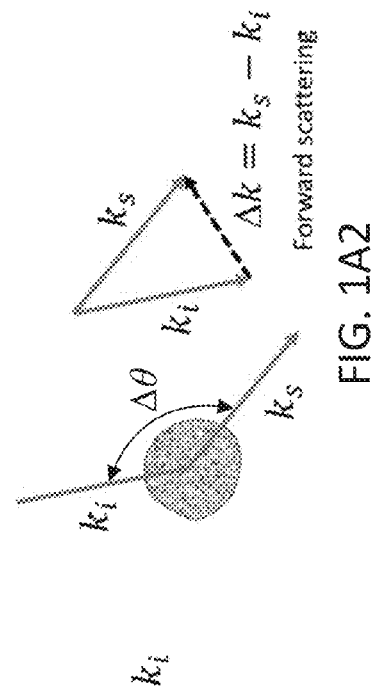
FIG. 1A1
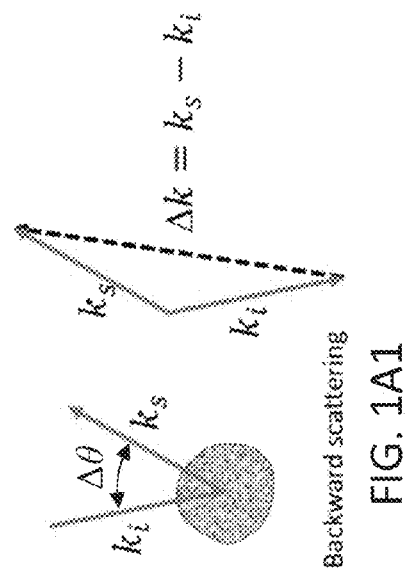
FIG. 1A2
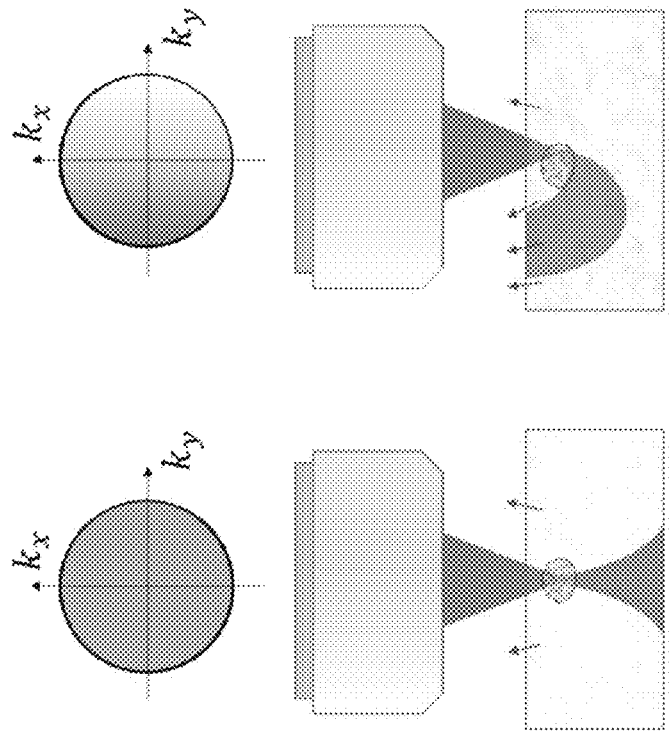
FIG. 1B1
FIG. 1B2
FIG. 1B3

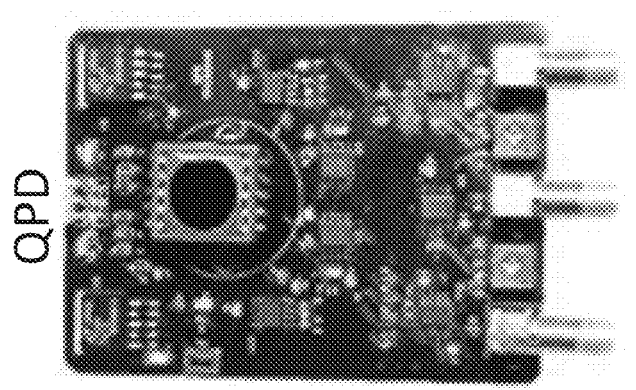
FIG. 8B2
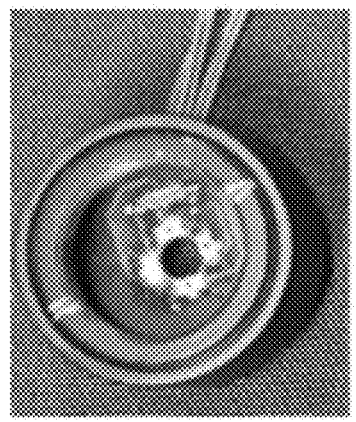
FIG. 9
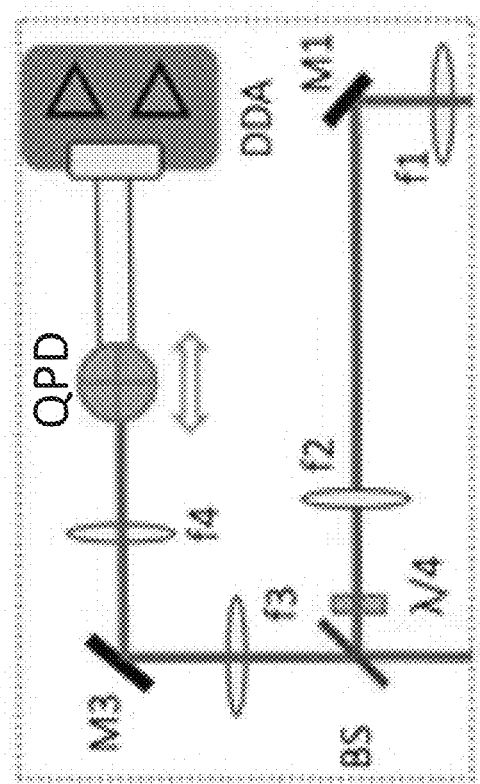
FIG. 8B1

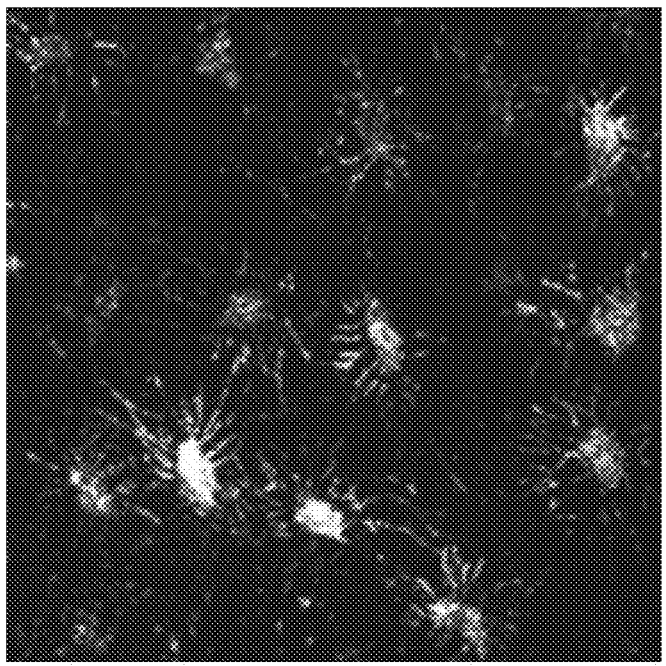
FIG. 10B2
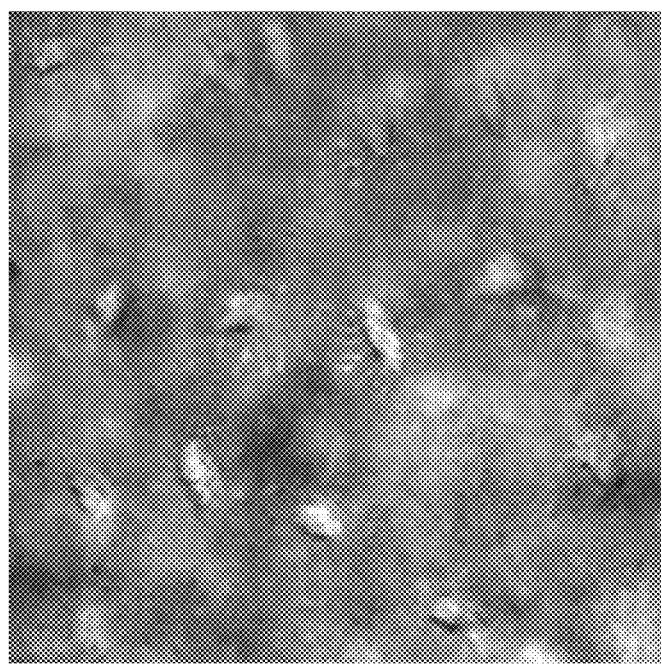
FIG. 10B1

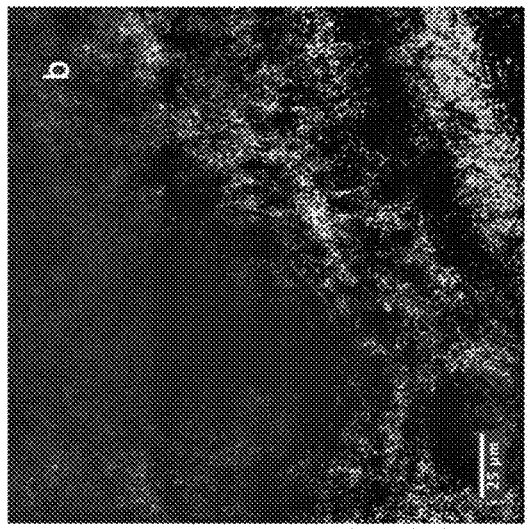
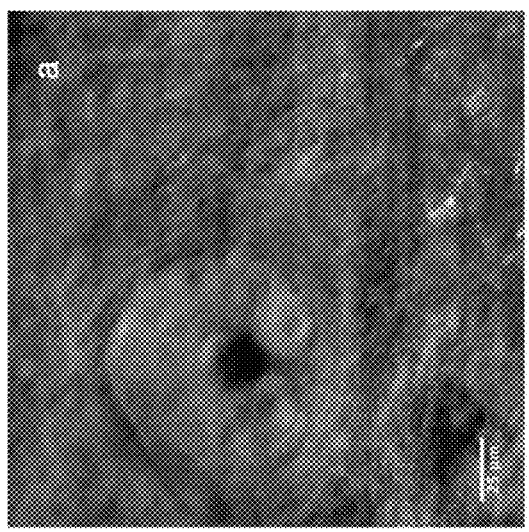
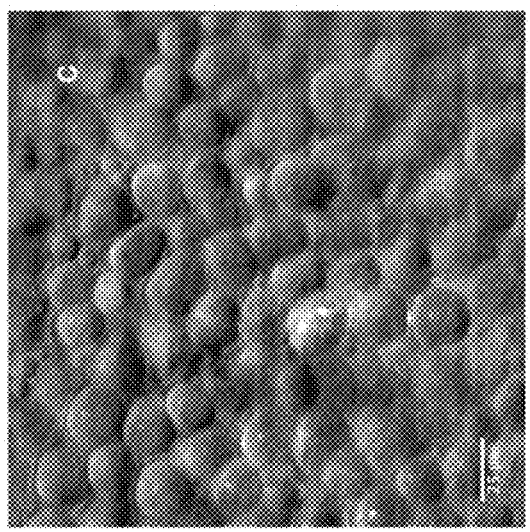
FIG. 11

SYSTEMS, METHODS, AND APPARATUS FOR DIFFERENTIAL PHASE CONTRAST MICROSCOPY BY TRANSOBJECTIVE DIFFERENTIAL EPI-DETECTION OF FORWARD SCATTERED LIGHT

CROSS-REFERENCE TO RELATED APPLICATIONS

This application is based on, claims the benefit of, and claims priority to U.S. Provisional Patent Application No. 62/796,703 filed on Jan. 25, 2019, and U.S. Provisional Patent Application Ser. No. 62/892,621 filed on Aug. 28, 2019. Each of the preceding application is hereby incorporated herein by reference in its entirety for all purposes.

STATEMENT REGARDING FEDERALLY SPONSORED RESEARCH

This invention was made with government support under grant number FA9550-17-1-0277 awarded by the Department of Defense. The government has certain rights in the invention.

BACKGROUND

Differential interference contrast (DIC) microscopy is a decades-old technique that provides contrast in unstained samples by bringing out subtle refractive index differences, and has been used for label-free imaging of cells and thin biological specimens. However, DIC operates in the transmission geometry in which light is provided from a first side of a sample, transmitted through the sample, and impinges on a detector placed on the other side of the sample. DIC microscopy images phase objects in transparent samples by detecting small phase differences of two closely-spaced light paths propagating through the phase object. In a conventional DIC microscope, the phase difference is detected. interferometrically using a detector placed in transmission geometry, opposite to the side of illumination. DIC is not compatible with imaging scattering samples such as thick biological tissues, however, because the phase of the transmitted light is not preserved after undergoing multiple scattering events. In addition, placement of detectors behind the tissue is not always possible, especially for imaging whole intact organisms, as the light cannot penetrate through the entire thickness of the sample.

Differential phase contrast (DPC) scanning laser microscopy provides images similar to DIC. but does not require polarization optics and can be performed in tandem with other point scanning modalities such as confocal and multiphoton microscopy. Instead of a wide-field camera, DPC employs split detectors placed on the opposite side of the sample in a conventional transmission geometry. Accordingly, while obtaining DIC- or DPC-like images in thick biological samples would be extremely useful for clinical and preclinical imaging, placing an optical detector on the other side of an in vivo sample is nearly always impossible because of limited light penetration through the scattering tissue. For years, it has not been possible (and not for lack of trying by practitioners in the field) to obtain DIC- or DPC-like images when the detectors are constrained to be on the same side of the sample as the illumination.

Until recently, thick tissue imaging has been undertaken using techniques such as reflectance confocal microscopy (RCM) and optical coherence tomography (OCT) that detect directly backscattered photons while rejecting multiply scattered photons using a confocal pinhole in RCM, or a coherence gate in OCT.

More recently, oblique back illumination microscopy (OBM) techniques were developed in which a light source can be placed on the same side of the sample as detectors. Unlike RCM and OCT, which can detect only sharp refractive index changes and often suffer from speckle noise, OBM can detect slow refractive index variation in biological tissue, and does not have the same susceptibility to speckle noise. In the originally proposed wide-field OBM implementation, the oblique back illumination was provided by two optical fibers arranged on the sides of an objective lens, alternately providing illumination from the two sides that were back scattered and captured through the objective lens to generate a differential contrast image on a camera. In a later-proposed scanning OBM implementation, the illumination was delivered through the objective lens, while two or more optical fibers were placed such that the face of the optical fiber collects light just to the side of the objective lens, to collect light from the tissue after multiple scattering, and guide the light to the detectors to generate the differential signal. While such a system can facilitate generation of DPC-like images of in vivo samples, the optical arrangement is cumbersome, and difficult to operate consistently as the signals from the two optical fibers must be balanced to generate the differential signal. Due at least in part to these difficulties, clinical implementations of scanning OBM systems using optical fiber detectors have not yet been realized.

Accordingly, systems, methods, and apparatus for differential phase contrast microscopy by transobjective differential epi-detection of forward scattered light are desirable.

SUMMARY

In accordance with some embodiments of the disclosed subject matter, systems, methods, and apparatus for differential phase contrast microscopy by transobjective differential epi-detection of forward scattered light are provided.

In accordance with some embodiments of the disclosed subject matter, a system for transobjective differential epi-detection of forward scattered light is provided, the system comprising: a scanning microscope comprising: a light source; an optical train defining an optical path of the scanning microscope having an optical axis comprising: scanning components optically coupled to the light source and configured to scan a beam from the light source across a surface of a sample; and a microscope objective optically coupled to the scanning components ; and a detector mechanically coupled to the scanning microscope along the optical path within a first distance of a pupil plane of the optical train, the detector comprising: a printed circuit board defining a central clear aperture having a center configured to coincide with the optical axis of the optical path; a first photodiode mechanically coupled to the printed circuit board at a first radial distance from the center; and a second photodiode mechanically coupled to the printed circuit board at the first radial distance from the center and on an opposite side of the central aperture from the first photodiode, wherein the first distance is less than or equal to twice the first radial distance; an amplifier electrically coupled to the detector, comprising: a first transimpedance amplifier configured to receive a first current signal from the first photodiode and provide a first voltage signal as an output; a second transimpedance amplifier configured to receive a second current signal from the second photodiode and provide a second voltage signal as an output; a differential detection amplifier configured to receive the first voltage signal and the second voltage signal, and provide a third voltage signal indicative of a difference between the first current signal and the second current signal as an output; and at least one hardware processor that is programmed to: cause the light source to emit a beam of light toward the sample via the optical train; cause the scanning components to scan the beam of light across the sample; receive, from the differential detection amplifier, a plurality of output signals, each of the plurality of output signals indicative of a structure of the sample at location at which the beam was focused; generate an image based on the plurality of output signals; and cause the image to be presented using a display.

In some embodiments, the detector is integrated within the microscope objective.

In some embodiments, the detector is mounted between the microscope objective and the second plurality of lenses, the detector further comprising: a housing supporting the printed circuit board; first threads configured to receive the microscope objective; and second threads configured to mechanically couple the housing to the scanning microscope.

In some embodiments, the central aperture has a diameter of about 5 millimeters.

In some embodiments, the system further comprises a confocal imaging system comprising: a half wave plate having a first side optically coupled to the light source, and a second side; a polarizing beam splitter having a first port optically coupled to the second side of the half wave plate, a second port optically coupled to a confocal imaging arm, and a third port optically coupled to the scanning components, and an interface that passes light having a first polarization and redirects light having a second polarization; and a quarter wave plate having a first side optically coupled to the scanning components, and a second side optically coupled to the objective lens; wherein the hardware processor is further programmed to: receive, from the confocal imaging arm, confocal reflectance imaging data indicative of a structure of the sample at locations at which the beam was focused; and generate a second image based on the confocal reflectance imaging data in parallel with the image based on the plurality of output signals.

In some embodiments, the system further comprises a plurality of lenses configured to optically generate a conjugate pupil plane within the optical path, wherein the detector is mounted within the first distance of the conjugate pupil plane.

In some embodiments, the scanning components comprise: a first galvanometer optically coupled to the microscope objective; and a polygon scanner or a second galvanometer, the polygon scanner or the second galvanometer optically coupling the light source to the first galvanometer.

In accordance with some embodiments, a microscope objective is provided, comprising: a housing having a first end and a second end, the second end comprising mounting threads; a plurality of optical components defining an optical axis, the plurality of optical components comprising: an objective lens mounted at the first end, the objective lens configured to collect light from a sample placed in a field of view of the objective lens, wherein the plurality of optical components create a pupil plane at a first axial distance along the optical axis at which rays having the same angle of incidence on the objective lens from the within the field of view converge at the same radial distance from the optical axis; a first photodetector mounted within the housing at a second axial distance along the optical axis and offset from the optical axis by a first radial distance; and a second photodetector mounted within the housing at the second axial distance along the optical axis and offset from the optical axis by the first radial distance in a direction opposite from the first photodetector.

In some embodiments, the second axial distance is equal to the first axial distance.

In some embodiments, the microscope objective further comprises a physical aperture collocated with the pupil plane, wherein the first photodetector and the second photodetector are mechanically coupled to the physical aperture.

In some embodiments, the microscope objective further comprises a printed circuit board defining a central aperture having a center, wherein the printed circuit board is mounted within the housing such that the center coincides with the optical axis, and wherein the first photodetector and the second photodetector are mechanically coupled to printed circuit board, and electrically coupled to the first printed circuit board.

In some embodiments, the microscope objective further comprises an amplifier electrically coupled to the printed circuit board, comprising: a first transimpedance amplifier configured to receive a first current signal from the first photodiode and provide a first voltage signal as an output; a second transimpedance amplifier configured to receive a second current signal from the second photodiode and provide a second voltage signal as an output; a differential detection amplifier configured to receive the first voltage signal and the second voltage signal, and provide a third voltage signal indicative of a difference between the first current signal and the second current signal as an output.

In some embodiments, the microscope objective further comprises, the printed circuit board acts as a physical aperture of the microscope objective and is collocated with the pupil plane.

In some embodiments, the first radial distance is in a range of 2 millimeters (mm) to 10 mm.

In accordance with some embodiments of the disclosed subject matter, a detection apparatus for transobjective differential epi-detection of forward scattered light is provided, the detection apparatus comprising: a housing configured to be mechanically coupled to a scanning microscope such that the housing is disposed along an optical path of the scanning microscope; a substrate having a first surface and a second surface and an aperture defined by a through-hole from the first surface to the second surface, the substrate mounted within the housing; a first photodetector mechanically coupled to the first surface of the substrate and disposed at a first distance from a side of the aperture; and a second photodetector mechanically coupled to the first surface of the substrate and disposed at the first distance from an opposite side of the aperture from the first photodetector, such that second photodetector is separated from the first photodetector by the diameter of the aperture and twice the first distance.

In some embodiments, the housing is a microscope objective barrel.

In some embodiments, the substrate comprises a printed circuit board, and the first photodetector and the second photodetector are mechanically coupled to printed circuit board, and electrically coupled to the first printed circuit board..

In some embodiments, the detection apparatus further comprises an amplifier electrically coupled to the printed circuit board, the amplifier comprising: a first transimpedance amplifier configured to receive a first current signal from the first photodiode and provide a first voltage signal as an output; a second transimpedance amplifier configured to receive a second current signal from the second photodiode and provide a second voltage signal as an output; a differential detection amplifier configured to receive the first voltage signal and the second voltage signal, and provide a third voltage signal indicative of a difference between the first current signal and the second current signal as an output.

In some embodiments, the first distance is in a range of 0.5 millimeters (mm) to 1 mm.

In some embodiments, the detection apparatus further comprises: a third photodetector mechanically coupled to the first surface of the substrate and disposed at the first distance from a perpendicular side of the aperture to the side along which the first photodetector is disposed; and a fourth photodetector mechanically coupled to the first surface of the substrate and disposed at the first distance from an opposite side of the aperture from the third photodetector.

In some embodiments, a system for differential epi-detection of forward scattered light suitable for label free in vivo flow cytometry is provided, the system comprising: a scanning microscope comprising: a first light source configured to emit light at a first wavelength; a second light source configured to emit light at a second wavelength; an optical train defining an optical path of the scanning microscope having an optical axis comprising: scanning components optically coupled to the light source and configured to scan a beam from the light source across a surface of a sample and a microscope objective optically coupled to the scanning components; and a detector arranged to receive light emitted by the first light source and the second light source that has been directed into a sample via the microscope objective, forward scattered through the sample, and re-emitted from the sample on the same side as the microscope objective, the detector comprising: at least one pair of photodiodes optically coupled to detect forward scattered light emitted from the sample toward a first side of the microscope objective and a second side of the microscope objective that is opposite the first side; an amplifier electrically coupled to the detector, comprising: a differential amplifier configured to receive a first signal and a second signal from the at least one pair of photodiodes indicative of the intensity of light received at the first side of the microscope objective and the second side of the microscope objective at the first wavelength, respectively, and provide a signal indicative of a difference between the first signal and the second signal as an output; and a sum amplifier configured to receive a third signal and a fourth signal from the at least one pair of photodiodes indicative of the intensity of light received at the first side of the microscope objective and the second side of the microscope objective at the second wavelength, respectively, and provide a signal indicative of a sum of the first signal and the second signal as an output; and at least one hardware processor that is programmed to: cause the first light source to emit a first beam of light toward a sample via the optical train; cause the second light source to emit a second beam of light toward a sample via the optical train; cause the scanning components to scan the first beam of light and the second beam of light across the sample; receive, from the differential amplifier, a first plurality of output signals, each of the plurality of output signals indicative of a structure of the sample at a location at which the first beam was focused; receive, from the sum amplifier, a second plurality of output signals, each of the plurality of output signals indicative of an absorption by the sample at a location at which the second beam was focused; and generate image data indicative of the presence of blood cells and leukocytes in the sample based on the first plurality of output signals and the second plurality of output signals.

In some embodiments, the detector is mechanically coupled to the scanning microscope along the optical path within a first distance of a pupil plane of the optical train, and the detector comprises: a printed circuit board defining a central aperture having a center configured to coincide with the optical axis of the optical path; and the at least one pair of photodiodes comprises: a first pair of photodiodes configured to inhibit detection of light of the second wavelength, the first pair of photodiodes comprising: a first photodiode mechanically coupled to the printed circuit board at a first radial distance from the center; a second photodiode mechanically coupled to the printed circuit board at the first radial distance from the center and on an opposite side of the central aperture from the first photodiode, wherein the first distance is less than or equal to twice the first radial distance; and a second pair of photodiodes configured to inhibit detection of light of the first wavelength, the second pair of photodiodes comprising: a third photodiode mechanically coupled to the printed circuit board at the first radial distance from the center; a fourth photodiode mechanically coupled to the printed circuit board at the first radial distance from the center and on an opposite side of the central aperture from the third photodiode.

In some embodiments, the first wavelength is in a range including near infrared light and excluding visible light, and the second wavelength is in a range including visible light and excluding near infrared light.

BRIEF DESCRIPTION OF DRAWINGS

The patent or application file contains at least one drawing executed in color. Copies of this patent or patent application publication with color drawing(s) will be provided by the Office upon request and payment of the necessary fee.

Various objects, features, and advantages of the disclosed subject matter can be more fully appreciated with reference to the following detailed description of the disclosed subject matter when considered in connection with the following drawings, in which like reference numerals identify like elements.

FIG. 1A1 shows an example of a backward scattering event and an associated scattering wave vector in k-space.

FIG. 1A2 shows an example of a forward scattering event and an associated scattering wave vector in k-space.

FIG. 1B1 shows an example of forward scattered light exiting from the face of a sample into which the light entered after multiple forward scattering events, and the distribution of the scattered light intensity in k-space at the pupil plane.

FIG. 1B2 shows an example of less forward scattered light exiting from the face of a sample into which the light entered after multiple forward scattering events due to the incidence angle of the phase object, and the distribution of the scattered light intensity in k-space at the pupil plane.

FIG. 1B3 shows another example of forward scattered light exiting from the face of a sample into which the light entered after multiple forward scattering events, and the distribution of the scattered light intensity in k-space at the pupil plane.

FIG. 2 shows an example of a system for differential phase contrast microscopy by transobjective differential epi-detection of forward scattered light in accordance with some embodiments of the disclosed subject matter.

FIG. 3 shows an example of an apparatus for differential phase contrast microscopy by transobjective differential epi-detection of forward scattered light in accordance with some embodiments of the disclosed subject matter.

FIG. 8B1 shows an example of an extended pupil plane system for differential phase contrast microscopy by transobjective differential epi-detection of forward scattered light implemented in accordance with some embodiments of the disclosed subject matter.

FIG. 8B2 shows an example of a quadrature photodiode detection apparatus that can be used in connection with an extended pupil plane system for differential phase contrast microscopy by transobjective differential epi-detection of forward scattered light in accordance with some embodiments of the disclosed subject matter.

FIG. 9 shows an example of an apparatus for differential phase contrast microscopy by transobjective differential epi-detection of forward scattered light implemented in accordance with some embodiments of the disclosed subject matter.

FIGS. 10B1 and 10B2 show an example image of in-vivo osteocytes in mouse bone generated using mechanisms described herein for differential phase contrast microscopy by transobjective differential epi-detection of forward scattered light, and an image of the in-vivo osteocytes in mouse bone generated using confocal reflectance microscopy techniques.

FIG. 11 shows examples of in vivo mouse ear skin generated using mechanisms described herein for differential phase contrast microscopy by transobjective differential epi-detection of forward scattered light, and corresponding images generated using confocal reflectance microscopy techniques.

DETAILED DESCRIPTION

Figure 2:
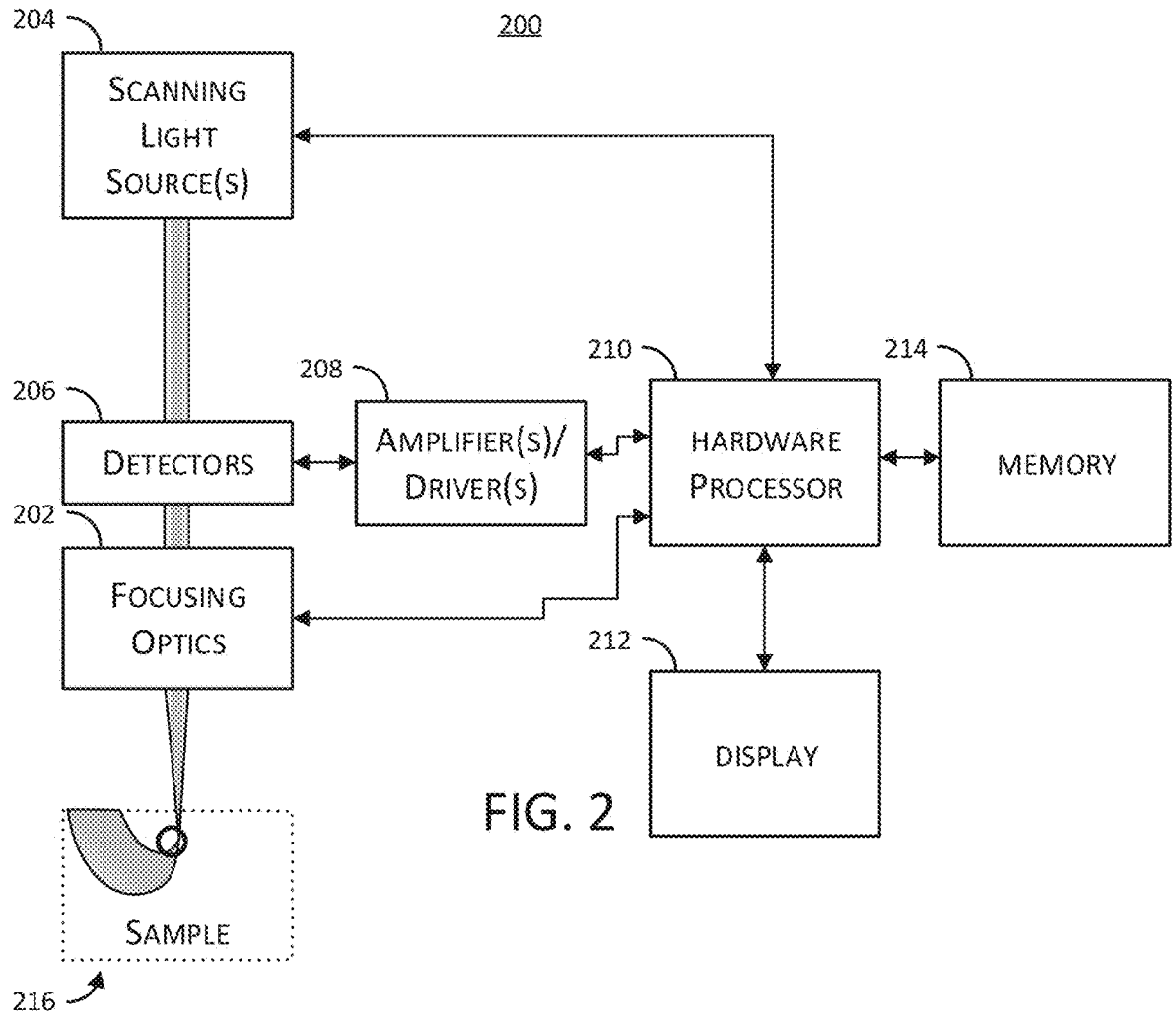

In accordance with some embodiments of the disclosed subject matter, mechanisms (which can include systems, methods, and media) for differential phase contrast microscopy by transobjective detection of forward scattered light are provided.

In accordance with some embodiments of the disclosed subject matter, mechanisms described herein can utilize a detector or detectors placed at a particular radial distance from the optical axis within a plane of an imaging system other than imaging plane to determine one or more properties of an object being imaged. By contrast, in conventional imaging systems, an image of an object is formed at the image plane, and the information at the image plane is detected by area sensor in a wide-field imaging system (e.g., an array of pixels, such as a 2D array of CCD or CMOS pixels), by a single pixel photodetector with a pinhole in a confocal scanning imaging system, by a human observer, etc. At the imaging plane of a conventional imaging system, all of the rays of light received form a single point in the scene are focused at a single point, regardless of the path that the ray took. Many imaging systems, such as microscopes, have one or more pupil planes (sometimes referred to as the hack focal plane of a particular portion of the optics of the system) at which all light that entered the imaging system at a particular angle converges at a particular radial distance from the optical axis. A simplified example of a microscope objective pupil plane is described below in connection with FIG. 4.

In scanning imaging system, scanning of the illumination beam is generally realized via angular tilt with the beam configured to remain stationary at the pupil plane (e.g., the axis of the tilt is about the pupil plane). As described below in connection with FIGS. 1B1 to 1B3, light from the scanning beam can enter a sample and he forward scattered multiple times such that it exits from same face of tissue into which the beam was directed. Due to refractive index variation at the focus, the forward scattered light experiences an angular tilt away from the optical axis, and after multiple scattering, exits the sample surface with an uneven brightness distribution as well as an uneven angular distribution. As described above, a tilt in the angle at which a ray intersects the image plane or the object plane transforms into a lateral shift in the pupil plane (e.g., a radial shift toward or away from the optical axis,). Similarly, a lateral shift of the point at which a ray intersects the image plane or the object plane transforms into a tilt in the pupil plane. In some embodiments, the mechanisms described herein can use the multiple detectors around the pupil aperture at the pupil plane to detect a beam shift in the exiting light, and form a differential phase-gradient image using information detected at various locations across the sample.

In some embodiments, mechanisms described herein can use a pair (or multiple pairs) of photodetectors placed within the optical path of an imaging system to detect the refractive index gradient along a specific orientation (or multiple specific orientations). For example, mechanisms described herein can use information detected by a pair of photodetectors arranged at the pupil plane of a microscope objective around the pupil aperture of the objective at a particular radial distance, such that the photodetectors detect light at a particular radial distance from the optical axis of the microscope objective. In such an example, if the photodetectors are placed on the object side of the aperture, the photodetectors can detect light that would otherwise be blocked by the pupil aperture of the microscope objective, and thus can detect information without blocking light that can be used to form an image at the image plane of the microscope.

As another example, mechanisms described herein can use information detected by a pair of photodetectors arranged at a conjugate of an initial pupil plane of an imaging system (e.g., a conjugate of the objective pupil plane), such as a secondary pupil plane, an intermediate pupil plane, an exit pupil, etc.

As yet another example, mechanisms described herein can use information detected by a pair of photodetectors arranged near an initial pupil plane of an imaging system (e.g., the objective pupil plane) or a conjugate of the initial pupil plane. In such an example, the photodetectors can be placed at a radial distance from the optical axis that is based on the distance from the pupil plane, and the angle at which the light diverges from the pupil plane, which can be determined based on the rear focal length of the lens or lenses that formed the pupil plane.

As still another example, mechanisms described herein can use information detected by any suitable number of photodetectors arranged at an extended pupil plane of an imaging system (e.g., created within an alternate optical path from a path of the scanning optics). In such an example, the photodetectors can be placed at the pupil plane and can completely obstruct the optical path to intercept all or substantially all of the light at the extended pupil plane.

In some embodiments, detection of light at a particular radial distance from the optical axis by a pair of opposing photodetectors can be referred to as the pupil plane differential detection (P2D2) microscopy, and does not require polarization optics, a confocal pinhole, or descanning, yet can produces images that are free of speckle and interference noise.

In some embodiments, mechanisms described herein can use two pairs of photodetectors offset by ninety degrees around the optical axis at an extended pupil plane. Additionally, in some embodiments, a beam splitter can be arranged near the pupil plane of the objective to separate scattered light from illumination light. In such embodiments, the full pupil aperture can be used to detect the scattered light.

Image formation based on detection of light at the pupil plane does not require de-scanning, which decreases the light throughput, and corresponding decreases signal to noise ratio. Additionally, pupil plane detection can occur prior to any polarization optics, scanning, and scanning lenses by occurring inside the objective lens or just after the object lens, and can avoid noise created by such components. In some embodiments, pupil plane detection can be implemented as an add-on apparatus to an existing scanning system that can be used to provide a phase-gradient label-free image in addition to, or in lieu of, images provided by the existing scanning system.

In some embodiments, the mechanisms described herein can be implemented using an annular printed circuit board (PCB) with one or more pairs of photodetectors on opposing sides of a central aperture. In such embodiments, the circuit board can be mechanically coupled to a scanning microscope such that the photodetectors receive light at or near the pupil plane. For example, the PCB can be mounted within a housing that can be configured to mechanically couple a microscope objective to the microscope system (e.g., with female threads to accept the object and male threads to fasten the housing to the microscope system). As another example, the PCB can be integrated into a microscope objective.

In some embodiments, the aperture size of the PCB can be equal to the size of the pupil aperture of the microscope objective. Additionally, the photodetectors can be electrically coupled to output circuitry, such as a trans-impedance amplifier and differential-amplifier board that can be used to generate a phase-gradient signal.

In some embodiments, mechanisms described herein can be used to generate a diffraction limited phase gradient image using photodetectors at the pupil plane. In a scanning microscope, multiple forward scattered light exits from the same face of sample after multiple scattering with a preferred tilt angle with respect to the microscope objective, and accordingly can be expected to arrive at a particular radial distance from the optical axis at the pupil plane of the microscope objective based on the principle that the tilt angle at the object plane is transformed into a radial shift at the pupil plane. A tilt at sample plane causes the intensity of light at the detectors in the pupil plane to be unbalanced, producing a differential signal. If there are no scattering events at the focus of the scanning beam, the paired detectors have the same intensity, and the differential detection rejects background scattered light of uniform intensity, and does not receive light scattered back at sharp angles because that light is closer to the optical axis at the pupil plane.

In some embodiments, mechanisms described herein can be used to detect directly back scattered light from the sample, that has been scattered at a particular tilt direction, as the tilt at the object plane is transformed into a lateral shift in the pupil plane which can then be detected by photodetectors. For example, in samples that include material that will cause sufficient backscattering, mechanisms described herein can detect the backscattered light that intersects the objective lens at a particular angle, such that it is present at a particular location within the pupil plane.

In some embodiments, mechanisms described herein can use any suitable number of pairs of detectors to generate image data indicative of the sub-surface structure of a sample. For example, in some embodiments, a single pair of photodetectors can be used to generate a single difference signal that can be used to generate image data. As another example, in some embodiments, two pairs of photodetectors offset by ninety degrees can be used to generate two difference signals that can be used to generate image data. In such an example, because the pairs are offset by ninety degrees, the two signals can be used to generate phase gradient signals at orthogonal directions. As still another example, in some embodiments, multiple pairs of photodetectors can be used to generate difference signals for different wavelengths of light (e.g., using pairs of photodetectors that are sensitive to different wavelengths).

In some embodiments, different types of detectors can be more suitable for different types of applications. For example, a detection apparatus that includes one or more pairs of photodetectors arranged around a central aperture can be placed directly at or near the pupil plane of the microscope objective. As another example, a detection apparatus that includes photodetectors in a quadrature arrangement without an aperture can be placed directly in the optical path at an extended pupil plane created using optics to create an alternate path from the microscope objective. In such an example, such a detection apparatus placed at the extended pupil plane can generate a higher quality signal with less noise because of the larger area for light collection.

In some embodiments, mechanisms described herein can be used to generate images indicative of the sub-surface structure of an in vivo issue sample. For example, mechanisms described herein for transobjective detection of forward scattered light can be used to generate DIC-like phase-gradient images of thick scattering tissue via a microscope objective. In some embodiments, mechanisms described herein can be used in many applications, such as clinical and preclinical healthcare and research applications.

For example, conventional blood cell analysis is an invasive procedure that requires extraction of a patient's blood, followed by ex-vivo analysis using a flow cytometer or hemocytometer. Blood extraction is often unpleasant and inconvenient, and is especially so inconvenient in infants and patients who are in critical pathological condition. Accordingly, mechanisms described herein can be used to generate images suitable for in vivo flow cytometer based on epi-collection of forward scattered light for label free detection of circulating blood cells and identification of leukocytes. A flow cytometer implemented in accordance with some embodiments of the disclosed embodiments can use real-time phase contrast and absorption contrast imaging channels to detect circulating blood cells and identification of leukocytes.

In some embodiments, as described above, differential epi-detection of forward scattered light can be used to generate high contrast image of tissues with small refractive index variation. Additionally, a sum of epi-detection signals of forward scattered light (e.g., at a wavelength at which light is differentially absorbed by hemoglobin) can be used to detect local absorption. For example, a differential phase contrast channel can be operated at a near-infrared wavelength (e.g., 925 nanometers (nm), 975 nm), and a sum absorption contrast channel can be operated at visible illumination near the hemoglobin absorption band (e.g., ~540-600 nm). As another example, differential phase contrast channel can be operated at a near-infrared wavelength (e.g., 925 nanometers (nm), 975 nm), and a sum absorption contrast channel can be operated at visible, ultraviolet, or infrared illumination wavelength that is absorbed preferentially by melanin as compared to other tissue or water (one example being ~490 nm, however many other examples exist due to the very broad absorbance spectrum of melanin) to investigate the presence of pigmented lesions.

In some embodiments, mechanisms described herein can detect forward scattered light at near-infrared wavelengths to generate real-time difference signals using a high-speed analog single processing and amplification system that facilitates generation of phase contrast imaging that can be used to detect circulating blood cells in vivo.

In some embodiments, mechanisms described herein can detect forward scattered light at visible wavelengths in a hemoglobin absorption band to generate real-time sum signals using a high-speed analog single processing and amplification system that facilitates absorption contrast imaging and can be used to label red blood cells in vivo. In some embodiments, mechanisms described herein can collect data that can be used to calculate the difference and sum signals for a particular portion of a sample simultaneously, and can utilize a combination of phase contrast image data generated from difference signals and absorption image data generated from sum signals that to generate high resolution phase contrast image data that can be used for blood cell counting and absorption contrast imaging for leukocytes counting by counting cells that are not labeled in hemoglobin absorption contrast images as leukocytes. In some embodiments, mechanisms described herein can include a near-infrared laser source and a suitable visible laser source for multicolor illumination, and can include a detection apparatus that is configured to detect forward scattered light that exits the same side of the sample into which the light is introduced at both wavelengths. For example, a PCB with multiple pairs of photodetectors can be placed at or near the pupil plane or a conjugate pupil plane, with different pairs of photodetectors configured to be sensitive to light at different wavelengths (e.g., a first pair being sensitive at the near infrared wavelength and not at the visible wavelength, and another pair being sensitive at the visible wavelength and not at the near infrared wavelength). As yet another example, a pair of multimode optical fibers can be attached to each side of an objective, with one of the pair configured to detect the visible light and the other to detect the near infrared light (e.g., via a filter on the optical fiber, or a filter on the detector). As yet another example, light from a pair of single optical fibers placed on opposite sides of an objective to collect forward scattered light from the sample surface can be separated using a dichroic filter(s). As a further example, forward scattered light emitted by the sample can be directed to pairs of near-infrared photodetectors and visible photodetectors (e.g., via optical fibers and a splitter, via the objective and a pupil plane detector, etc.). Note that, in some embodiments, the different colors of light can be multiplexed using various different techniques. For example, multiple detectors that are sensitive to different wavelengths can be used to detect the light simultaneously. As another example, a frame can be divided into time slots, and each light source can operate in a particular time slot, and thus the imaging can be interleaved to capture an image with a first color using the detectors in a first portion of the frame, and capture an image with a second color using the same detectors in a second portion of the frame. In such an example, images can be captured at 60 frames per second, but each color can be captured at only thirty frames per second by alternating colors of illumination. Colors can be alternated using any suitable Scheme, such as by frame, by line (e.g., odd lines can be capture in a first color, and even colors can be captured in another color in a first frame, and vice versa in a next frame).

Each year, millions of children die because of infection. Neonatal deaths account for 40 percent of all deaths among children under age five. An accurate blood cell count and leukocyte count are very important parameters for determining whether intervention is appropriate. However, because of impracticalities of invasive blood cell analysis procedures, especially in infants and patients who are in critical pathological condition, frequent analysis is often deemed unjustified in many patients that may benefit from more frequent analysis. While several noninvasive optical imaging techniques have been proposed for in vivo blood analysis, all of them have shortcomings in practice. RCM imaging can detect only sharp refractive index variation and suffers from speckle noise, which makes it poorly suited to detecting blood cells and blood flow. OCT can acquire cross-sectional images at high speed, but often has limited optical resolution. Third harmonic generation (THG) imaging requires high laser power that may exceed the ANSI safety guideline, which is a particular concern in the case of infants. Raman scattering-based imaging techniques are complex, and it is currently not possible to build a practical clinical device. Additionally, none of preceding techniques can differentiate leukocytes from red blood cells. In some embodiments, mechanisms described herein can be used to implement a compact flow cytometer that generates real-time image data that that is indicative of the presence of blood cells, and differentiates between leukocytes and red blood cells. For example, mechanisms described herein can be used to implement a hand held, low power (e.g., <10 mW laser power), and noninvasive blood parameter analyzing device. In an example implementation described below using a conventional polygon-galvo scanning system, and a data acquisition system described herein, a frame rate of at least 120 frames per second and at least 33 thousand lines per second was observed, which is sufficient for recording blood cell flow in skin.

FIGS. 1A1 and 1A2 show examples of a backward scattering event and a forward scattering event, and associated scattering wave vectors in k-space. In FIGS. 1A1 and 1A2 $k_i$ and $k_s$ are wave vectors of incident and scattered light, respectively. As shown in FIG. 1A1, scattering wave vector $\Delta k$ is large and along the axial direction for the backward scattering event. Only a sharp refractive index change along the direction of propagation or small scattering objects can generate a large wave vector along the axial direction. By contrast, the scattering wave vector $\Delta k$ is relatively small and along the transverse direction for the forward scattering event, which can be caused by larger objects with smaller and/or more gradual changes in refractive index. Accordingly, techniques that can reject backward scattered light and/or preferentially detect forward scattered light, such as techniques described herein for transobjective detection of forward scattered light can be used to visualize subtle refractive index variations in thick biological tissues, and can be used to generate DIC-like images.

Figure 3:
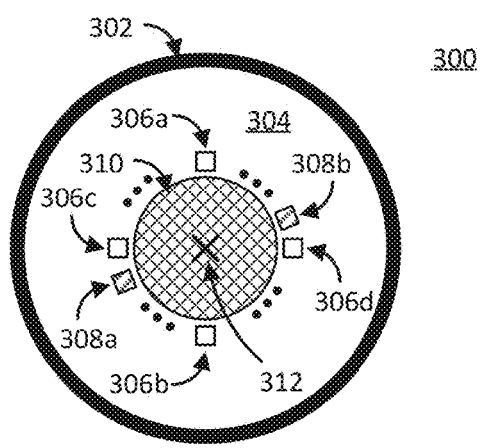

FIGS. 1B1 to 1B3 show examples of forward scattered light exiting from the face of a sample into which the light entered after multiple forward scattering events, and the distribution of the scattered light intensity in k-space at the pupil plane. Principles underlying differential phase-gradient imaging can be better understood by considering a phase object illuminated by a focused beam, as shown in FIGS. 1B1 to 1B3. As shown in FIGS. 1A1 and 1A2, in accordance with the size and direction of the scattering wave vector $\Delta k$, the cone of forward scattered light is tilted by an angle $\Delta\theta$. After additional multiple scattering events, a portion of forward scattered light can re-emerge from the same face of the sample, as shown in FIGS. 1B1 and 1B3. The intensity distribution of the emergent light on the surface is dependent on the initial forward scattering angle $\Delta\theta$ imposed by the phase object at the focus. As described herein, differential detection of scattered light can be used to produce phase-gradient image data when the detectors are placed in or near a pupil plane of an imaging system (e.g., a microscopy system, an ophthalmoscope, etc.).

As described above, in addition to eliminating the need to place optical fibers near the sample surface adjacent to the objective lens, in a telecentric scanning imaging system, the scanning beam pivots in the pupil plane and thus the pupil plane has a special relationship to the scanning beam. Beam translation at the sample plane is transformed into beam tilting at the pupil plane, making the beam laterally stationary at the pupil plane. When the initially forward scattered light exits from the face of tissue after multiple scattering, its intensity redistribution is accompanied by an angular tilt of the re-emergent light. Just as a shift in the image plane transforms into a tilt in the pupil plane, a tilt in the image plane transforms into a shift in the pupil plane due to the two planes being a Fourier conjugate pair. FIGS. 1B1 to 1B3 illustrate a beam tilt in the image plane and its corresponding beam shift in the Fourier plane using k-space diagrams. A k-vector in the Fourier plane corresponds to a tilt angle $\theta$ by the relation $k=2\pi n \sin\theta/\lambda$, where n is the refractive index of the medium, and $\lambda$ is the wavelength of light. The maximum tilt that the objective lens can accept is given by the k-vector $|kNA|$ where NA is the numerical aperture of the objective lens. A non-uniform angular distribution of scattered light at the sample plane produces a non-uniform intensity distribution at the pupil plane. By placing multiple detectors around the pupil aperture, the intensity difference across the pupil can be measured. Accordingly, a differential phase-gradient image can be produced by scanning a laser beam, as in a conventional laser scanning microscope, and detecting the intensity difference across the pupil using mechanisms described herein.

FIG. 2 shows an example 100 of a system for differential phase contrast microscopy by transobjective differential epi-detection of forward scattered light in accordance with some embodiments of the disclosed subject matter. As shown, system 200 can include focusing optics (e.g., a microscope objective), one or more scanning light sources 204; detectors 206; amplifiers and/or drivers associated with detectors 206; a hardware processor 210 configured to control operations of system 200 which can include any suitable hardware processor (which can be a microprocessor, digital signal processor, a microcontroller, an image processor, a GPU, a frame grabber, etc.) or combination of hardware processors; a display 212, and memory 214. Although not shown, system 200 can include an input device (such as one or more buttons, a microphone, a touchscreen, etc.) for accepting input from a user and/or from the environment; one or more signal generators; a communication system or systems for allowing communication between hardware processor 210 and other devices, such as a smartphone, a wearable computer, a tablet computer, a laptop computer, a personal computer, a game console, a server, etc., via a communication link. In some embodiments, memory 214 can raw data generated by detectors 206, difference signals generated from the raw data, image data generated by hardware processor 210, etc. Memory 214 can include a storage device (e.g., a hard disk, a Blu-ray disc, a Digital Video Disk, RAM, ROM, EEPROM, etc.) for storing a computer program for controlling hardware processor 210. In some embodiments, memory 214 can include instructions for causing hardware processor 210 to execute processes associated with the mechanisms described herein, such as processes described below in connection with FIGS. 7 and 13.

In some embodiments, focusing optics 202 can be any suitable optics for forming an image of a sample 216, forming a Fourier conjugate pair (e.g., at the pupil plane) of an image of sample 216, and/or projecting light toward additional optical components that can be used to generate an image of sample at an image plane of system 200. For example, focusing optics 202 can be an objective lens, such as a microscope objective that includes multiple lenses. As another example, focusing optics 202 can be an objective lens for an ophthalmoscope.

In some embodiments, scanning light source 204 can be any suitable light source or combination of light sources that can be configured to emit coherent light suitable for forward-scattering imaging, and suitable components for scanning the light over a portion of a sample. In some embodiments, light source 204 can emit light at any suitable wavelength, such as visible wavelengths, near infrared wavelengths, infrared wavelengths, etc. In a more particular example, light source 204 can be a diode laser that emits light centered around 648 nm. As another more particular example, light source 204 can be a 950 nm femto second laser or a 975 nm continuous wave laser.

In some embodiments, detectors 206 can be implemented as pairs of photodetectors positioned on opposing sides of an aperture that is configured to be positioned to coincide with an optical axis of focusing optics 202. In some embodiments, detectors can be any suitable type of photodetector, such as a photodiode, a pinned photodiode, a phototransistor, an avalanche photodiode, a single photon avalanche diode (SPAD), a quantum dot photodiode, etc. In some embodiments, detectors 206 can be implemented as CMOS pixels or CCD pixels, with accompanying driving and/or readout circuitry.

In some embodiments, amplifiers and/or drivers 208 can be any suitable amplification and/or driving circuitry that can be used to generate signals from detectors 206. For example, drivers can be used to reset, bias, read, etc., detectors 206, and amplifiers 208 can be used to generate a signal suitable for output to hardware processor 210. Additionally, in some embodiments, other signal processing, such as one or more analog-to-digital circuits, frame grabbers, etc., can be used to generate information that be processed by hardware processor 210 and/or output to display 212. In some embodiments, amplifiers 208 can include a transimpedance amplifier per photodetector to convert a current signal to voltage, and a differential detection amplifier to determine the difference between the voltage signals, when detectors 206 output current signals. However, this is merely an example, and amplifiers can be implemented using any suitable technique or combination of technique based on the output of detectors 206. For example, in some embodiments, detectors 206 can generate voltage signals directly (e.g., via implantation as CMOS active-pixel sensors). In some embodiments, amplification components can be shared. For example, in some embodiments, photodetectors can be addressable, and can be read out individually or in pairs, and can use shared amplifier components. Note that communication links shown in FIG. 2, such as communication links between amplifiers 208 and hardware processor 210, hardware processor 210 and memory 214, hardware processor 210 and memory 212, etc., can be any suitable communication links or combination of links. For example, in some embodiments, such links can be such as wired links, such as links (e.g., one or more serial cable links, one or more coaxial cable links, one or more optical fiber links, etc.), or wireless links (e.g., Wi-Fi links, Bluetooth links, cellular links, free-space optical communication links such as IrDA links, etc.). In some embodiments, detector 206 and/or amplifiers 208 can receive power from any suitable source. For example, where a wired link is provided between detector 206 and/or amplifiers 208 and hardware processor 210, power can be provided over the wired link. As another example, where no wired link is provided between detector 206 and/or amplifiers 208 and hardware processor 210, power can be provided by a battery or another source of power that does not require a wired link.

In some embodiments, display 212 can be any suitable display device(s), such as a computer monitor, a touchscreen, a television, a transparent or semitransparent display, a head mounted display, etc., and/or input devices and/or sensors that can be used to receive user input, such as a keyboard, a mouse, a touchscreen, a microphone, a gaze tracking system, motion sensors, etc.

FIG. 3 shows an example 300 of an apparatus for differential phase contrast microscopy by transobjective differential epi-detection of forward scattered light in accordance with some embodiments of the disclosed subject matter. As shown in FIG. 3, apparatus 300 can include a housing 302, that can provide support for a substrate 304. In some embodiments, substrate 304 can be a printed circuit board and/or can provide support for a printed circuit board that is mechanically coupled to substrate 304. In some embodiments, substrate 304 can be used to position various photodetectors 306a, 306b, 306c, 306d, 308a, 308b, and/or any other suitable photodetectors. In some embodiments, any or all of photodetectors 306a to 306d, 308a, and 308b can be used to implement detectors 206.

As shown in FIG. 3, pairs of photodetectors 306a to 306d, 308a, and 308b can be provided on opposing sides of an aperture 310 that is centered on an optical axis 312. In some embodiments, apparatus 300 can be configured such that in operation optical axis 312 coincides with the optical axis of at least a portion of the optics of an imaging system that is used to generate data via photodetectors 306.

Although not shown, each photodetector in FIG. 3 can be electrically connected to one or more connection points that can be used to couple the photodetector to output circuitry (e.g., one or more amplifiers) and/or driving circuitry (e.g., bias circuitry, timing circuitry, etc.). Additionally, in some embodiments, such circuitry can be integrated into apparatus 300 in come embodiments. For example, one or more amplifiers can be mounted on substrate 304 and/or fabricated as part of photodetectors 306.

In some embodiments, different pairs of photodetectors can be configured to be sensitive to different wavelengths of light. For example, in FIG. 3, photodetectors 306a to 306d can be configured to be sensitive to a first range of wavelengths (e.g., infrared, near-infrared), and photodetectors 308a and 308b are sensitive to a different, non-overlapping range of wavelengths (e.g., visible light, blue light, red light, green light).

Note that although substrate 304 is shown as being substantially solid, this is merely an example, and one or more gaps can be formed in substrate 304, such as at a position at which electrical connection are not formed. For example, in some embodiments, the diameter of aperture 310 can be adjustable, and gaps can be formed to facilitate adjustment of the diameter such that the distance between opposing photodetectors is adjustable while maintaining the orientation of the photodetectors with respect to each other.

In some embodiments, the diameter of aperture 310 and/or the distance between opposing photodetectors (e.g., 306a and 306b, 306c and 306d, 308a, and 308b, etc.) can be any suitable distance. For example, the widest separation can be equal to diameter of the pupil or a conjugate pupil, as there is no light to detect outside the pupil diameter. Note that the pupil diameter or conjugate pupil diameter can be wider or narrower than the physical aperture diameter, and depends on the optics of the system forming the pupil. For example, as described below in connection with FIG. 8, optics can be included in the optical train that control a size of a conjugate pupil by creating a telescope within the optical train. To facilitate operation of the excitation beam and/or another imaging mode that operates through aperture 310, the diameter of aperture 310 can be maintained above a minimum threshold. For example, aperture 310 can have a minimum diameter that is about half the diameter of the pupil near which it is situated, as a smaller diameter can nearly totally obstruct the light source and/or light from the sample for another imaging modality. For example, if the pupil diameter is 6 mm, a distance between opposing photodetectors can be in a range of about 3 mm to about 6 mm (e.g., each photodetector can have a radial offset of about 1.5 mm to about 3 mm from the radial axis), and aperture 310 can similarly have a diameter in a range of about 3 mm to about 6 mm, depending on how closely the photodetectors are mounted to the edge of aperture 310. Note that pupil diameters of objectives have a wide range of values, and in some cases can be up to 20 mm in diameter, accordingly, aperture 310 can similarly be configured to have a diameter that is suitable for an objective with which it is being used.

Figure 4:
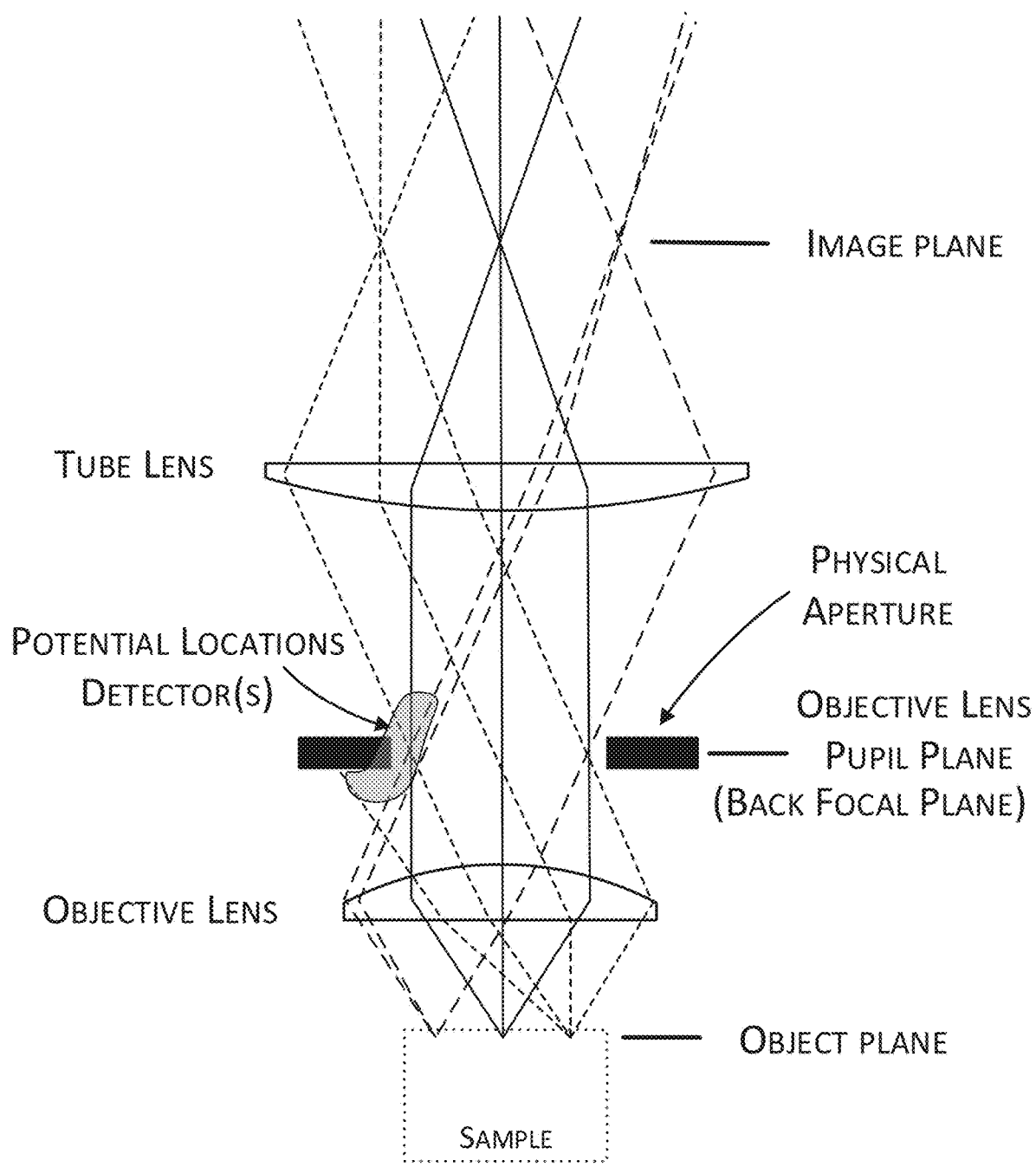
FIG. 4 shows an example of rays traversing a portion of an optical path of a simplified microscope and locations at which detectors can be placed to facilitate differential phase contrast microscopy by transobjective epi-detection of forward scattered light in accordance with some embodiments of the disclosed subject matter.

FIG. 4 shows an example of rays traversing a portion of an optical path of a simplified microscope and locations at which detectors can be placed to facilitate differential phase contrast microscopy by transobjective epi-detection of forward scattered light in accordance with some embodiments of the disclosed subject matter. As shown in FIG. 4, rays that intersect the objective lens at the same angle of incidence (note that all rays are shown in the sample plane in FIG. 4), converge at same radial distance from the optical axis at the objective lens pupil plane. The rays that intersect at 0° converge at the optical axis at the pupil plane, while rays that intersect at a steeper attack angle converge father from the optical axis. Note that rays that diverge from the same point on the sample at the pupil plane converge at the same point at the image plane. As shown in FIG. 4, photodetectors for transobjective differential epi-detection of forward scattered light can be placed in various locations within an optical system, to preferentially detect rays that intersect with the objective lens in a particular range of incidence angles, such as angles corresponding to multiple forward-scattered light from a thick tissue sample. Potential locations for such detectors are illustrated in FIG. 4 in the shaded area that corresponds roughly to the area in front of and around a physical aperture that is often associated with the objective at the pupil plane (e.g., to block light that enters objective lens at very steep angles from proceeding further). The precise positioning of the photodetectors can be based on the expected incidence angles of the light to be detected, and whether maintaining the numerical aperture of the optical system is desirable. For example, in a combined imaging system in which the central light is being used for a different imaging modality, maintaining the numerical aperture of the optical system is generally desirable, and consequently placement of photodetectors in front of the physical aperture may be most appropriate if possible. Alternatively, in an imaging system in which forward scattered light is the only imaging modality being used, detectors can be placed closer to the optical axis of the objective lens, while still permitting the light source to illuminate the sample. In some embodiments, such as embodiments in which a conventional objective lens is used, placement behind the pupil plane may be necessary due to physical inaccessibility of the pupil plane itself. This can reduce the numerical aperture of the system, but as described herein, can facilitate DCI-like imaging via the objective lens of thick tissue samples in vivo.

Figure 5:
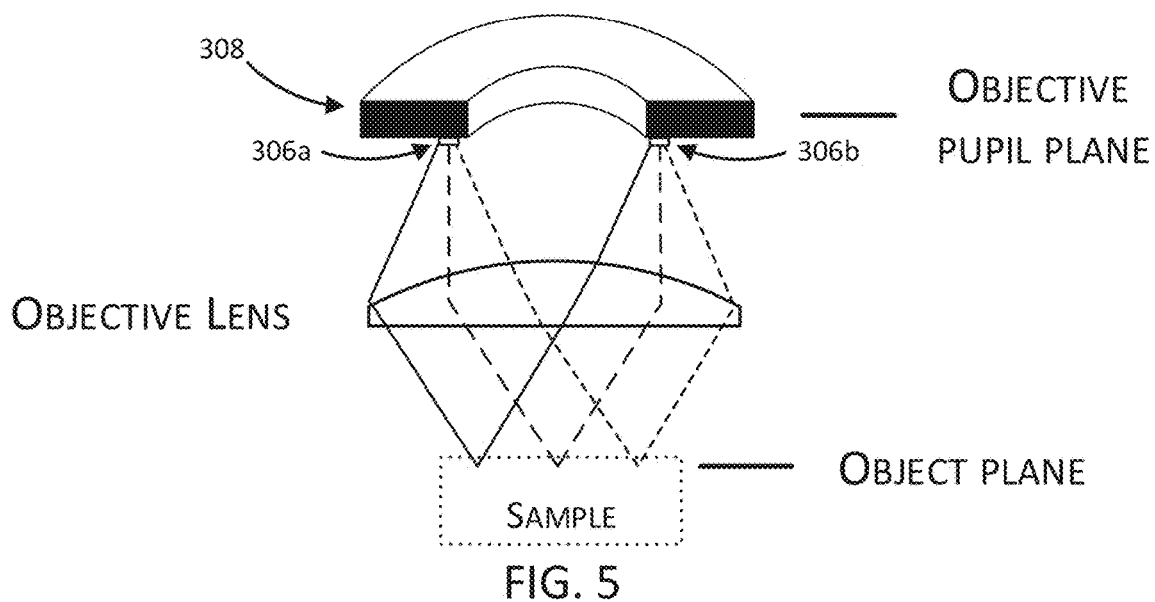
FIG. 5 shows an example of rays traversing a portion of an optical path of a simplified microscope and intersecting detectors placed near the pupil plane of the objective to facilitate differential phase contrast microscopy by transobjective epi-detection of forward scattered light in accordance with some embodiments of the disclosed subject matter.

FIG. 5 shows an example of rays traversing a portion of an optical path of a simplified microscope and intersecting detectors placed near the pupil plane of the objective to facilitate differential phase contrast microscopy by transobjective epi-detection of forward scattered light in accordance with some embodiments of the disclosed subject matter. As shown in FIG. 5, detectors 306a and 306b can be placed at the pupil plane or adjacent to but just in front of the pupil plane (i.e., on the sample side of the pupil plane), and can be supported by substrate 308, which can for example, be integrated into a microscope objective. As shown in FIG. 5, due to the placement of the detectors at the pupil plane, the detectors collect light emitted from all points across the sample that is emitted at a particular angle with respect to the objective lens so long as it is within the field of view of the objective lens.

Figure 6:
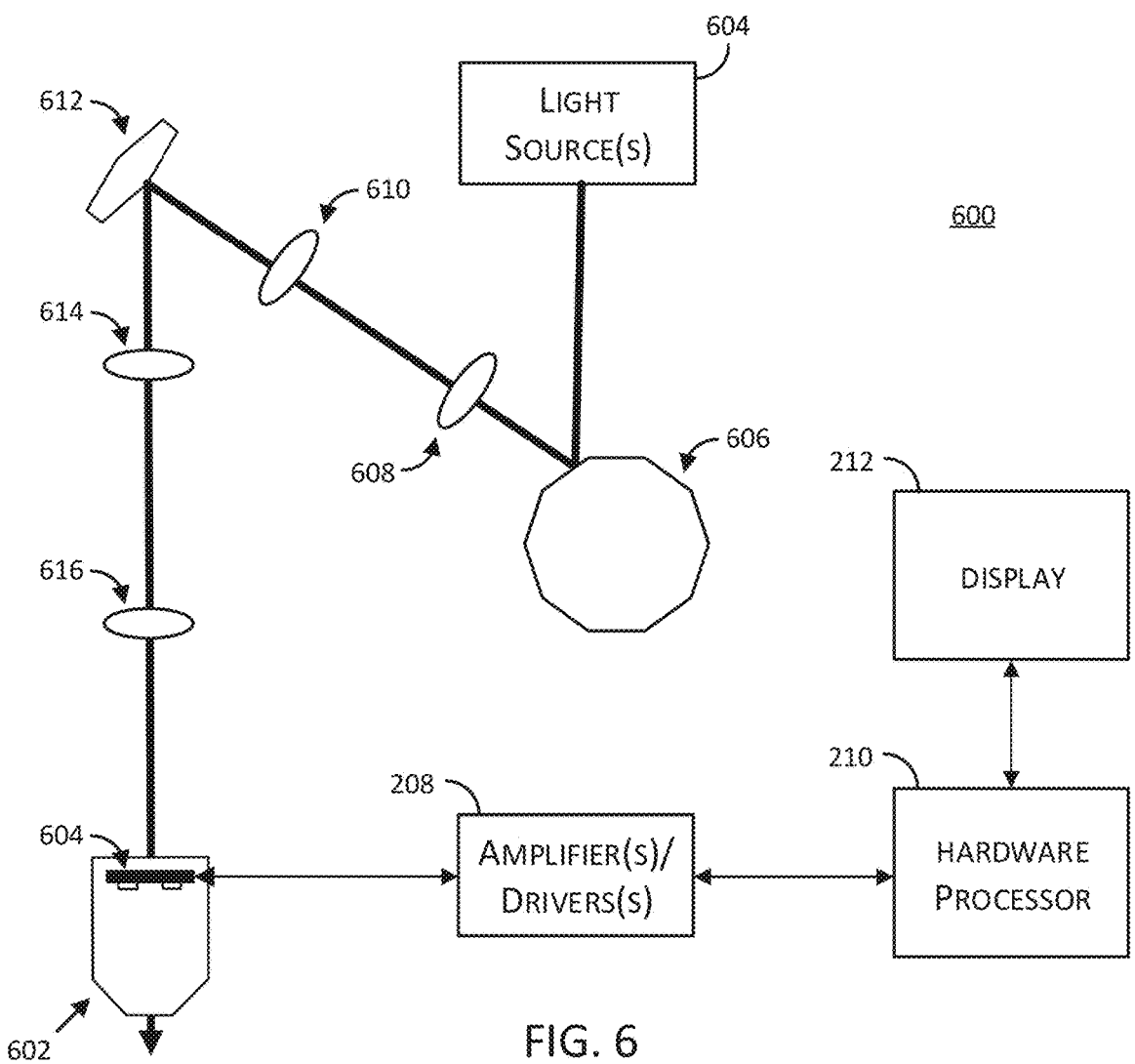
FIG. 6 shows another example of a system for differential phase contrast microscopy by transobjective differential epi-detection of forward scattered light in accordance with some embodiments of the disclosed subject matter.

FIG. 6 shows another example 600 of a system for differential phase contrast microscopy by transobjective differential epi-detection of forward scattered light in accordance with some embodiments of the disclosed subject matter. As shown in FIG. 6, system 600 can include a light source or multiple light sources 604, which can be used to emit a beam that is used to interrogate a sample. In some embodiments, light source 604 can emit a beam of light, which is reflected by a polygon scanner 606 toward a galvanometer 612 via lenses 608 and 610. In some embodiments, as polygon scanner 606 rotates, the beam is reflected at a slightly different angle, causing the beam to translate across the surface of a sample along a first axis. Polygon scanner 606 can have any suitable number of facets. For example, although shown with 10 facets for ease of observation, polygon scanner can have 36 or more facets. In some embodiments, galvanometer 612 can rotate as polygon scanner 606 rotates to cause the beam to scan along a second axis. For example, galvanometer 612 can rotate to cause the beam to translate across the surface of a sample along a second axis each time polygon scanner 606 rotates a certain number of times. Galvanometer 612 can redirect the beam toward objective 602 via lenses 614 and 616, and can direct the beam through an aperture in apparatus 604, which can serve as a physical aperture of objective 602. Note that the combination of polygon scanner 606 and galvanometer 612 is merely an example of scanning optical components that can be used to scan a beam across a surface of a sample via a microscope objective in a scanning microscope, and other scanning optical components can be used. For example, a pair of galvanometer mirrors can be used to provide such scanning with one controlling scanning in a first direction and the second controlling scanning in the orthogonal direction.

In some embodiments, apparatus 604 can be an implementation of apparatus 300 mounted within objective 602 at a pupil plane of objective 602. As described above, in some embodiments, polygon scanner 606 and galvanometer 612 can cause the beam(s) of light emitted by light source(s) to tilt at the pupil plane of objective 602, and objective 602 can focus the beam at various points of a sample, which can cause at least a portion of the light from the beam to be forward scattered until it is re-emitted toward objective 602. A portion of the forward scattered light can arrive at the objective lens of objective 602 at an incident angle that causes the light to arrive at one of the detectors of apparatus 604. In some embodiments, signals generated by detectors associated with apparatus 604 can be output to amplifiers and/or drivers 208, and can be processed (e.g., by hardware processor 210) and/or displayed. Although connections are not explicitly shown in FIG. 6, hardware processor 210 can control operation of polygon scanner 606 and galvanometer 612, for example, by providing control signals to cause polygon scanner 606 and/or galvanometer 612 to rotate.

Figure 7:
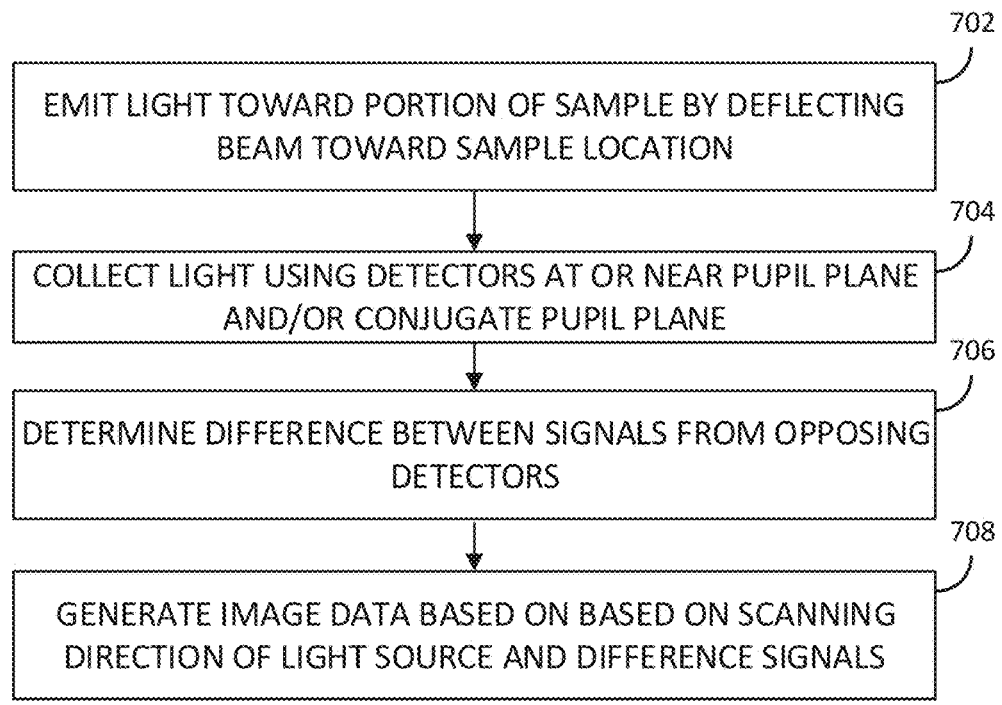
FIG. 7 shows an example of a process for differential phase contrast microscopy by transobjective differential epi-detection of forward scattered light in accordance with some embodiments of the disclosed subject matter.

FIG. 7 shows an example 700 of a process for differential phase contrast microscopy by transobjective differential epi-detection of forward scattered light in accordance with some embodiments of the disclosed subject matter. As shown in FIG. 7, process 700 can start at 702 by emitting light toward a portion of a sample by deflecting (or tilting) a beam toward a sample. For example, scanning components can be used to direct the beam through an objective lens at a particular location and angle such that the beam is focused at a particular position and depth of the sample.

At 704, process 700 can include collecting light using one or more detectors located at or near the pupil plane of the objective lens, and/or at a conjugate of the objective lens pupil plane. As described above, photodetectors can be placed at or near the pupil plane at a particular radial distance from the optical axis to collect light that was emitted from the sample (e.g., forward scattered light, backscattered light, fluoresced light, etc.) at a particular angle with respect to the objective lens.

At 706, process 700 can determine a difference between signals from opposing detectors. In some embodiments, any suitable techniques can be used to determine the difference between the signals from opposing detectors. For example, current signals from opposing photodiodes can be converted to voltage signals using transimpedance amplifiers, and the resulting voltages can be compared using a differential detection amplifier. In some embodiments, the magnitude of the difference signal can encode information about the composition of the sample at the point at which the beam was aimed when the detected light was emitted. For example, in a more homogenous portion of the sample, forward scattering will occur less often, and the signals can be expected to be more similar. As another example, when the beam focuses on the edge of a cell membrane, the transitions between the cell membrane and the surrounding material are more likely to cause forward scattering events in one direction than another based on the angle of incidence of the light, causing a pronounced difference in the signals between the photodetectors (which may depend on the alignment of the blood cell and photodetectors).

At 708, process 700 can generate image data based on scanning direction of the light source and the difference signals. In some embodiments, any suitable technique can be used to generate image data from the difference signals. For example, conventional linescan and framescan synchronization signals can be used to generate image frames using the difference signal, which can be converted to image data with a digitizer or frame grabber.

Figure 8A:
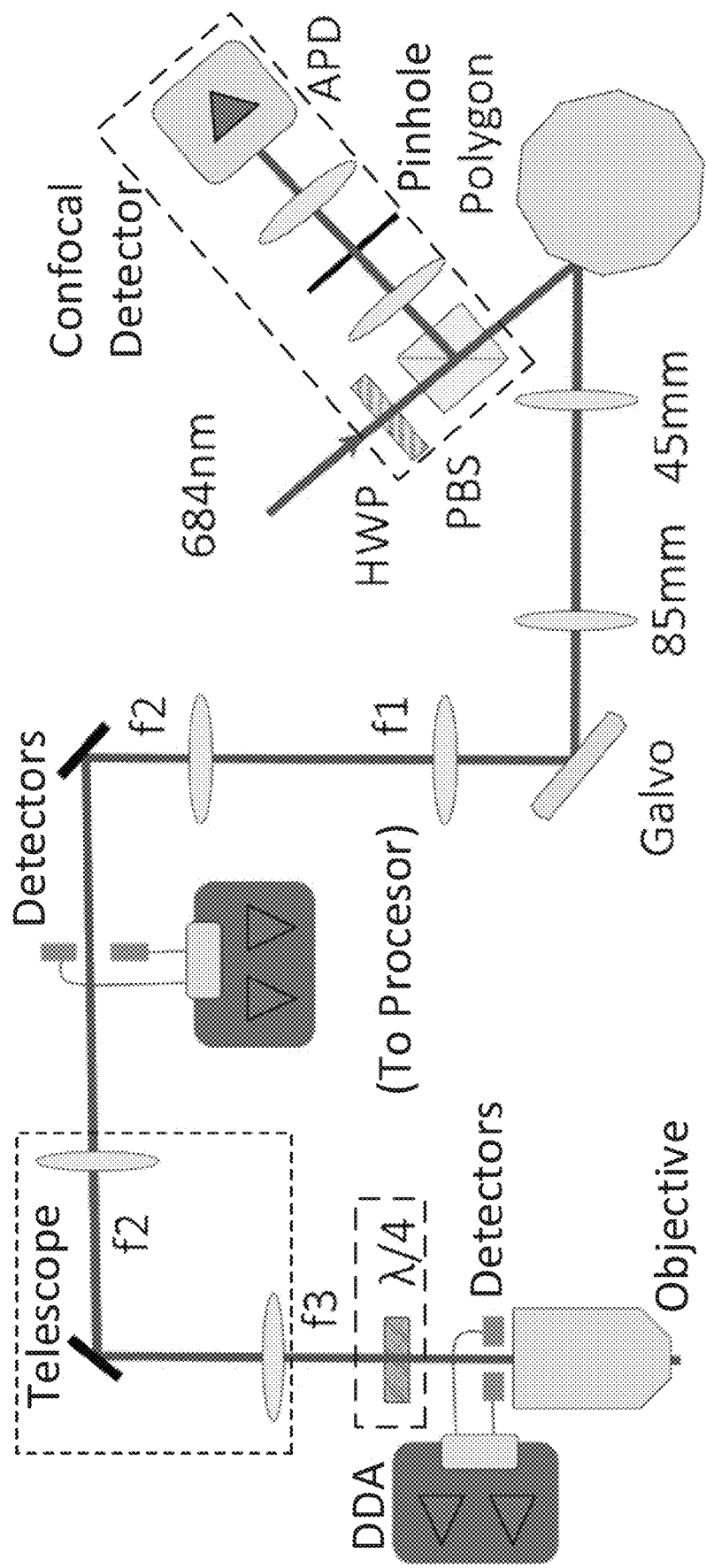
FIG. 8A shows multiple example systems for differential phase contrast microscopy by transobjective differential epi-detection of forward scattered light implemented in accordance with some embodiments of the disclosed subject matter.

FIG. 8A shows multiple example systems for differential phase contrast microscopy by transobjective differential epi-detection of forward scattered light implemented in accordance with some embodiments of the disclosed subject matter. The system shown in FIG. 8A combines transobjective differential epi-detection of forward scattered light with a confocal imaging arm that can be used simultaneously. Note that detectors are shown in FIG. 8A in two positions, near the pupil plane of the objective, and at a conjugate of the pupil plane. However, in practice, these were implemented in the alternative, not simultaneously. The system represented in FIG. 8A is a video rate scanning platform that includes a 648 nm diode laser that is available from Micro Laser Systems of Garden Grove, Calif. The laser power at the sample was limited to 5 milliwatts (mW) using a half waveplate (HWP) and a polarization beam splitter (PBS). A 36 facet polygon scanner (a Lincoln DT-36-275-040/SB12 from Cambridge Technology of Bedford, Mass.) was used for fast axis scanning, and a galvanometer mirror (a model 6240 galvanometer scanner from Cambridge Technology) was used for slow axis scanning. A confocal imaging arm was used to compare and complement images generated using mechanisms described herein with corresponding confocal reflectance images. A 25 micrometer (μm) pinhole was used to block scattered light, which is 0.6 times the airy disk size of the optical system of the system, and an avalanche photodiode (APD) was used to generate confocal reflectance imaging data. An Olympus 60×1.0 NA water immersion objective lens with a 6 mm diameter aperture was used as the objective. Four photodiodes (SFH 2701 photodiodes available from OSRAM Licht AG of Munich, Germany) were connected to a 15 megahertz (MHz) bandwidth custom built transimpedance amplifier and differential detection amplifier (DDA). Two imaging channels generated from the four photodiodes (one channel per pair of opposing photodiodes) and a confocal reflectance imaging channel were digitized using a 10 bit frame grabber (a Solios eAJXA Dual frame grabber available from Matrox Imaging of Dorval, Canada). The scan positions of the scanning beam on the sample were encoded in time, such that linescan and framescan synchronization signals that coincided with the scan position were used by the framegrabber to generate image frames. In this configuration, the detector was implemented as described below in connection with FIG. 9 with a 5 mm aperture, and placed in a conjugate pupil plane of the objective created by extending the imaging arm with a telescope, and mirrors. The 5 mm aperture of the ring detector reduced the excitation beam diameter at the objective lens back pupil to 3.75 mm. The detection pupil size at the ring detector was 8 mm, corresponding to 6 mm at the pupil of the object lens, based on the ratio of f2 to f3 shown in FIG. 9. For in vivo experiments, mice were anesthetized using isoflurane and placed on a 3-axis stage (a ROE200N stage available from Sutter Instrument of Novato Calif.) with a custom 3D printed mouse holder. All animal experiments were performed in accordance with the institutional guidelines for animal research. In the system represented in FIG. 8A, f1=100 mm, f2=200 mm, and f3=150 mm.

FIG. 8B1 shows an example of an extended pupil plane system for differential phase contrast microscopy by transobjective differential epi-detection of forward scattered light implemented in accordance with some embodiments of the disclosed subject matter. As shown in FIG. 8B1, an additional optical path was be created using a pellicle beam splitter (BS) to split both the illumination and the collection beam. A pair of lenses having focal lengths f3=75 mm and f4=50 mm were used to extend the objective lens pupil plane to an extended pupil plane at which a quad photodetector (QPD) was disposed at the extended pupil plane, and obstructed the additional optical path. Since the illumination beam is able to use the full pupil aperture, and the detector is not in the pathway of the scanning beam, the system shown in FIG. 8B1 has full resolution and full field-of-view.

FIG. 8B2 shows an example of a quadrature photodiode detection apparatus that can be used in connection with an extended pupil plane system for differential phase contrast microscopy by transobjective differential epi-detection of forward scattered light in accordance with some embodiments of the disclosed subject matter. Note that the photodiodes in the quadrature detection apparatus are large enough to capture light from the entire pupil created by the lenses shown in the system of FIG. 8B1

FIG. 9 shows an example of an apparatus for differential phase contrast microscopy by transobjective differential epi-detection of forward scattered light implemented in accordance with some embodiments of the disclosed subject matter. The apparatus shown in FIG. 9 includes an annular PCB supporting four photodiode detectors arranged around a 5 mm aperture. As the exact objective pupil plane is inside the objective lens and was inaccessible to mounting the detectors, the PCB was mounted within a 1" lens tube with an adaptor for mounting the objective. As shown in FIG. 8A, the apparatus shown in FIG. 9 was mounted for different experiments at a conjugate of the pupil plane that was generated by extending the imaging arm of the microscope using a telescope and mirrors (shown near the top of FIG. 8A), and behind the objective and offset from the objective pupil plane (shown on the left of FIG. 8A, but with the telescope removed). The photodetectors were connected to a custom-built differential detection amplifier, which generated two real-time phase contrast imaging channels. As described below in connection with FIGS. 10 and 11, techniques described herein were used to generate ex vivo images of mouse spinal cord and in vivo images of mouse ear skin.

Figure 10A:
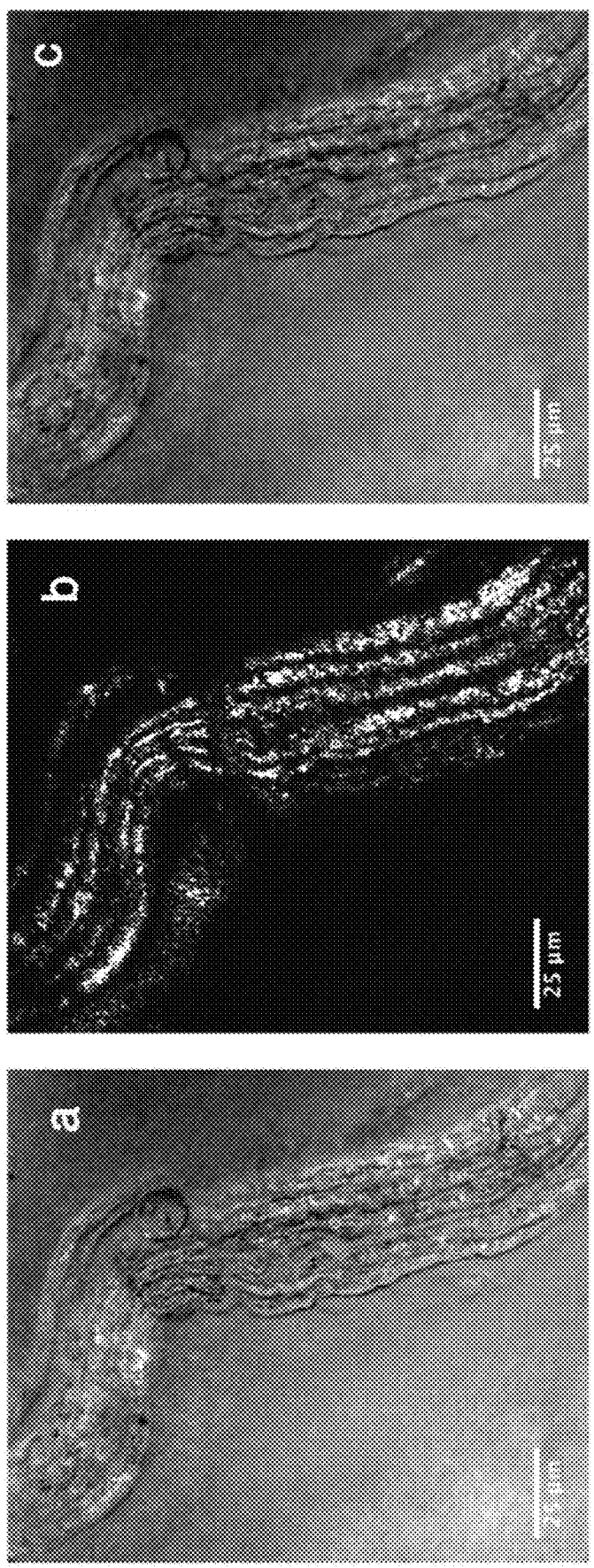
FIG. 10A shows an example image of an ex-vivo mouse spinal cord tissue slice generated using mechanisms described herein for differential phase contrast microscopy by transobjective differential epi-detection of forward scattered light, an image of the ex-vivo mouse spinal cord tissue slice generated using confocal reflectance microscopy techniques, and a composite combining information from both imaging modalities.

FIG. 10A shows an example image of an ex-vivo mouse spinal cord tissue slice generated using mechanisms described herein for differential phase contrast microscopy by transobjective differential epi-detection of forward scattered light, an image of the ex-vivo mouse spinal cord tissue slice generated using confocal reflectance microscopy techniques, and a composite combining information from both imaging modalities. As shown in FIG. 10A, panel (a) shows an ex-vivo image of a mouse spinal cord tissue slice generated using the system represented in FIG. 8A in which the detector apparatus shown in FIG. 9 was placed at the conjugate pupil plane. FIG. 10A panel (b) is a confocal reflectance image based on data that was generated using the confocal arm at the same time that the data used to generate the image in panel (a) was being generated. The image in FIG. 10A panel (c) is a composite image created by overlaying the confocal image in blue color on the image generated from the transobjective differential epi-detection of forward scattered light. Contrast in these images is generated primarily from the lipid-rich myelin sheaths surrounding nerve axons. These images show that the mechanisms described herein can detect lateral phase gradients and produce a DIC-like image in a scattering tissue (spinal cord) that is distinct from the RCM image.

FIGS. 10B1 and 10B2 show an example image of in-vivo osteocytes in mouse bone generated using mechanisms described herein for differential phase contrast microscopy by transobjective differential epi-detection of forward scattered light, and an image of the in-vivo osteocytes in mouse bone generated using confocal reflectance microscopy techniques. As shown in FIG. 10B1, the image of in-vivo osteocytes in mouse bone generated using the system represented in FIG. 8B1 in which the detector apparatus shown in FIG. 8B2 was placed at the extended pupil plane. FIG. 10B2 shows a confocal reflectance image based on data that was generated using the confocal arm shown in FIG. 8A at the same time that the data used to generate the image in FIG. 10B1 was being generated.

FIG. 11 shows examples of in vivo mouse ear skin generated using mechanisms described herein for differential phase contrast microscopy by transobjective differential epi-detection of forward scattered light, and corresponding images generated using confocal reflectance microscopy techniques. In a second experiment, the detector apparatus shown in FIG. 9 was placed after the objective lens of the system represented in FIG., near the objective pupil, even though the exact pupil plane is inaccessible. In this setting, the photodetectors of the detector apparatus were shifted away from the exact objective pupil plane by ~5 mm. In this configuration, a detector apparatus can be added to any existing microscope without additional modification. The images in FIG. 11 shows in vivo images of mouse (wild type C57BL/6) ear skin. Images in FIG. 11 panels (a) and (b) show the sebaceous gland around a hair follicle in the reticular dermis layer, approximately 50 µm below the surface of the mouse skin. The imaging depth of imaging based on transobjective differential epi-detection of forward scattered light depends on maintaining illumination beam focus in the scattering medium. With increasing depth, contrast is reduced as the point spread function is degraded. Accordingly, the penetration depth of techniques described herein for transobjective differential epi-detection of forward scattered light are similar to the penetration depth of confocal reflectance and other scanning phase gradient imaging techniques. The image in FIG. 11 panel (a) generated via transobjective differential epi-detection of forward scattered light shows much more detailed cellular structures, including the nucleus of the sebaceous gland cells and the granular structure of lipids, than the corresponding confocal reflectance image in FIG. 11 panel (b). Images in FIG. 11 panels (c) and (d) show adipocytes in the dermis layer of mouse skin, approximately 60 µm below the skin surface. The image in FIG. 11 panel (c) generated via transobjective differential epi-detection of forward scattered light shows DIC-like morphological features while the confocal reflectance image in FIG. 11 panel (d) shows only the highly backscattering structures. FIG. 11 support that the pupil plane detector does not necessarily need to be placed at the exact pupil plane, or even in particularly close proximity, as the 5 nun distance from the photodiodes to the pupil plane represents a relatively large fraction of the parfocal distance of the objective.

Note that when the photodetectors are shifted away from the pupil plane, the collection beam at the detectors change both with the imaging depth and the imaging field. For example, for the 60×1.0 NA objective lens used in the system represented in FIG. 8A, if the photodiodes are 5 mm away from the objective lens back pupil plane, the collection beam shifts by +/−0.16 mm laterally at the photodiode (due to the 5 mm offset from the pupil plane) corresponding to a +/−100 µm scanning of the illumination beam at the sample plane. Note that if the detector were placed at the pupil plane, the beam would have only tilted at the photodiode with no lateral shift. Further, if imaging depth is 50 µm below the surface, the beam diameter at the detector will be increased by ~0.19 mm. Thus moving the photodetectors away from the exact pupil plane results in a relatively small reduction in the illumination field-of-view, but otherwise has relatively little impact on the quality of the signal acquired by the detector. Restriction of the illumination pupil aperture by the detector apparatus reduced the resolution of the imaging system due to the detector apparatus partially blocking the optical pathway. The numerical aperture of the imaging system represented in FIG. 8A was reduced from 1.0 to 0.83 for the 60× objective. Placing detectors within the objective at the pupil plane (or otherwise in front of the physical aperture) can recover the full numerical aperture and full field-of-view of the microscope.

In some embodiments, the ability to place the photodetectors for transobjective differential epi-detection of forward scattered light directly after the objective lens, or inside the objective lens, can alleviate the need for descanning (e.g., as required in RCM), and can eliminate interference noise created by polarization optics, scanning lenses, and other components in the optical train. For these reasons, and other reasons described above, pupil plane detection can be a compact and inexpensive addition to a standard laser scanning microscope that can facilitate generation DIC-like images in thick tissue samples.

Figure 12:
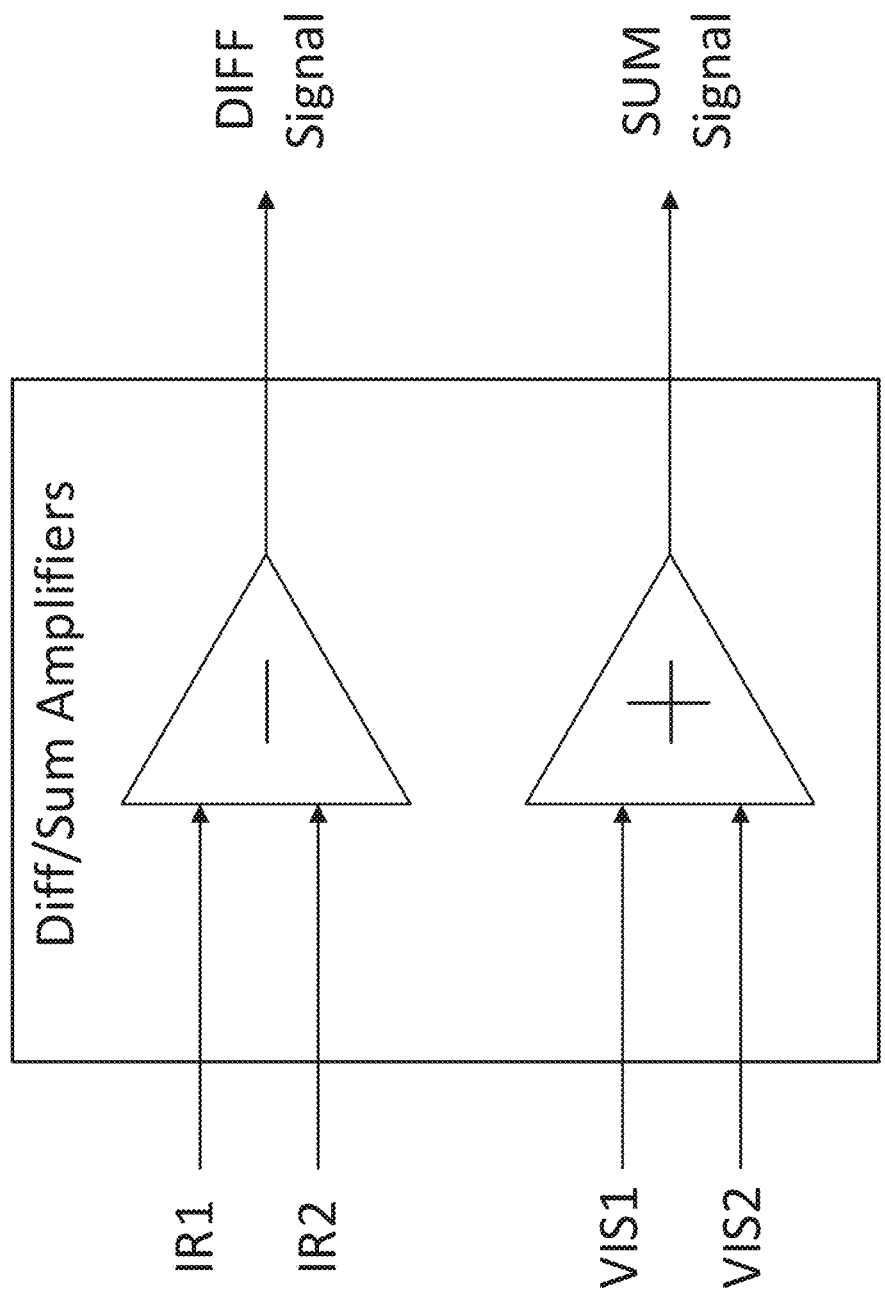
FIG. 12 shows an example of a portion of a signal processing technique that can be used to facilitate in vivo flow cytometry using signals generated via differential epi-detection of forward scattered light in accordance with some embodiments of the disclosed subject matter.

FIG. 12 shows an example of a portion of a signal processing technique that can be used to facilitate in vivo flow cytometry using signals generated via differential epi-detection of forward scattered light in accordance with some embodiments of the disclosed subject matter. As shown in FIG. 12, flow cytometry can be facilitated by generating a difference signal that represents phase contrast, and a sum signal that represents absorption contrast. In some embodiments, any suitable technique or combination of technique can be used to generate the input signals used to generate the difference signal and sum signal. For example, as described above, a first pair of infrared or near infrared detectors can be used to generate a pair of signals (IR1 and IR2) that can be used to generate a difference signal, and a second pair of visible light detectors can be used to generate a pair of signals (VIS1 and VIS2) that can be used to generate a sum signal.

In some embodiments, any suitable components can be used to implement the difference and sum amplifiers. For example, IR signals can be converted from current signals (e.g., if photodiodes are being used to generate the signals) using a transimpedance, and differential detection amplifier can be used to generate the difference signal (DIFF). As another example, VIS signals can combined as current signals, then converted to voltage signals and amplified for output. Alternatively, VIS signals can similarly be converted to voltage signals, and a summing amplifier can be used provide the sum signal (SUM). In some embodiments, additional signal conditioning can be applied, such as a high pass filter at each input, and a low pass filter at each output to reduce noise in the system.

Figure 13:
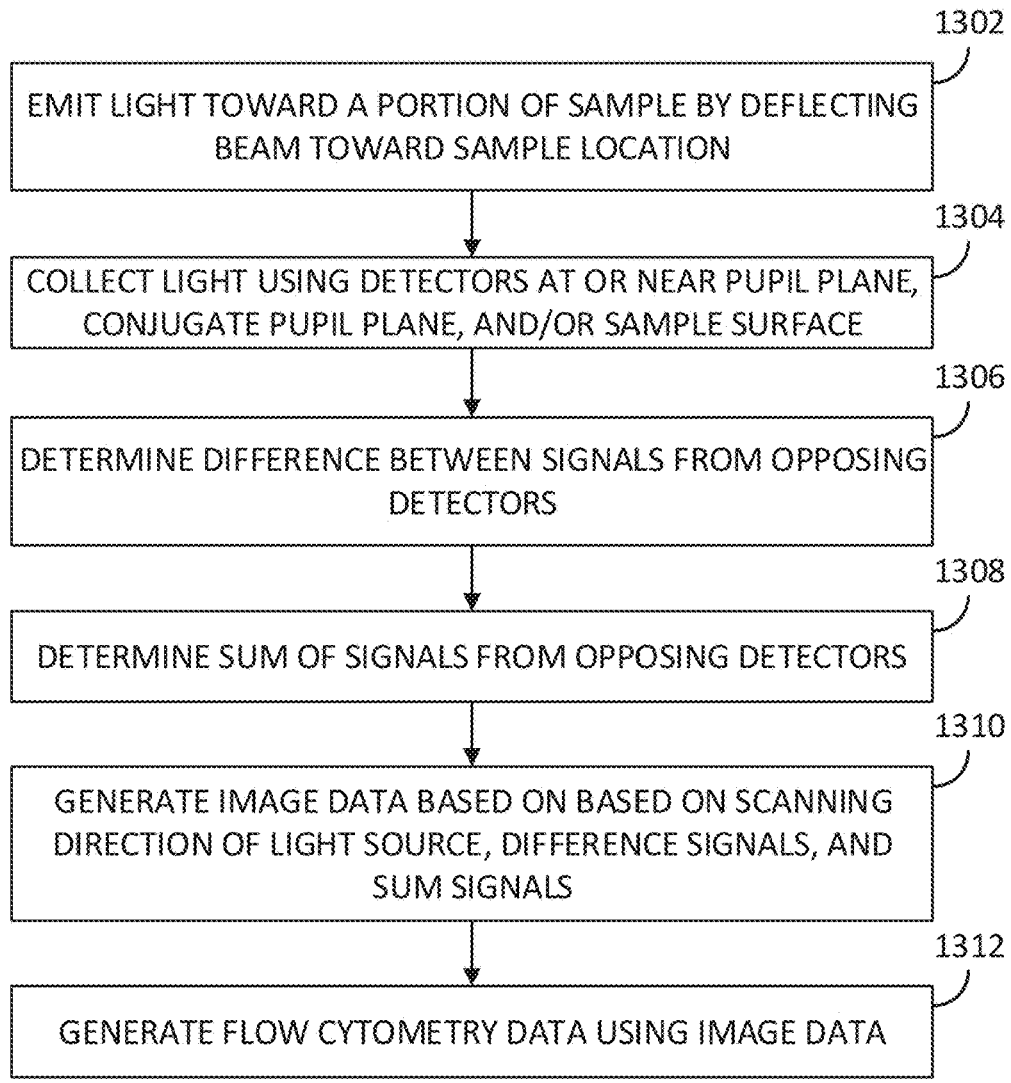
FIG. 13 shows an example of a process for in vivo flow cytometry using signals generated via differential epi-detection of forward scattered light in accordance with some embodiments of the disclosed subject matter.

FIG. 13 shows an example 1300 of a process for in vivo flow cytometry using signals generated via differential epi-detection of forward scattered light in accordance with some embodiments of the disclosed subject matter. As shown in FIG. 13, process 1300 can start at 1302 by emitting light toward a portion of a sample by deflecting (or tilting) a beam toward a sample. For example, scanning components can be used to direct the beam through an objective lens at a particular location and angle such that the beam is focused at a particular position and depth of the sample.

At 1304, process 1300 can include collecting light using one or more detectors located at or near the pupil plane of the objective lens, at a conjugate of the objective lens pupil plane, and/or near the sample surface via optical fibers. As described above, photodetectors can be placed at or near the pupil plane at a particular radial distance from the optical axis to collect light that was emitted from the sample (e.g., forward scattered light, backscattered light, fluoresced light, etc.) at a particular angle with respect to the objective lens. Additionally or alternatively, optical fibers can be placed adjacent to the sample to collect light that has been forward scattered multiple times and re-emitted back from the sample surface.

At 1306, process 1300 can determine a difference between signals from opposing detectors. In some embodiments, any suitable techniques can be used to determine the difference between the signals from opposing detectors, such as techniques described above in connection with 706 of FIG. 7. In some embodiments, the difference signal can represent the difference of signals detected at a particular wavelength or range of wavelengths, such as near infrared or infrared.

At 1308, process 1300 can determine a sum between signals from opposing detectors. In some embodiments, any suitable techniques can be used to determine the sum between the signals from opposing detectors, such as techniques described above in connection with FIG. 12. In some embodiments, the sum signal can represent the sum of signals detected at a particular wavelength or range of wavelengths, such as visible light or a particular relatively narrow band of visible light (e.g., corresponding to an absorbance spectrum of hemoglobin).

At 1310, process 1300 can generate image data based on scanning direction of the light source and the difference signals. In some embodiments, any suitable technique can be used to generate image data from the difference signals. For example, conventional linescan and framescan synchronization signals can be used to generate image frames using the difference signal, which can be converted to image data with a digitizer or frame grabber.

At 1312, process 1300 can generate flow cytometry data using the image data. For example, process 1300 can analyze the image data to determine a red blood cell count, blood flow, a white blood cell count, etc.

Figure 14:
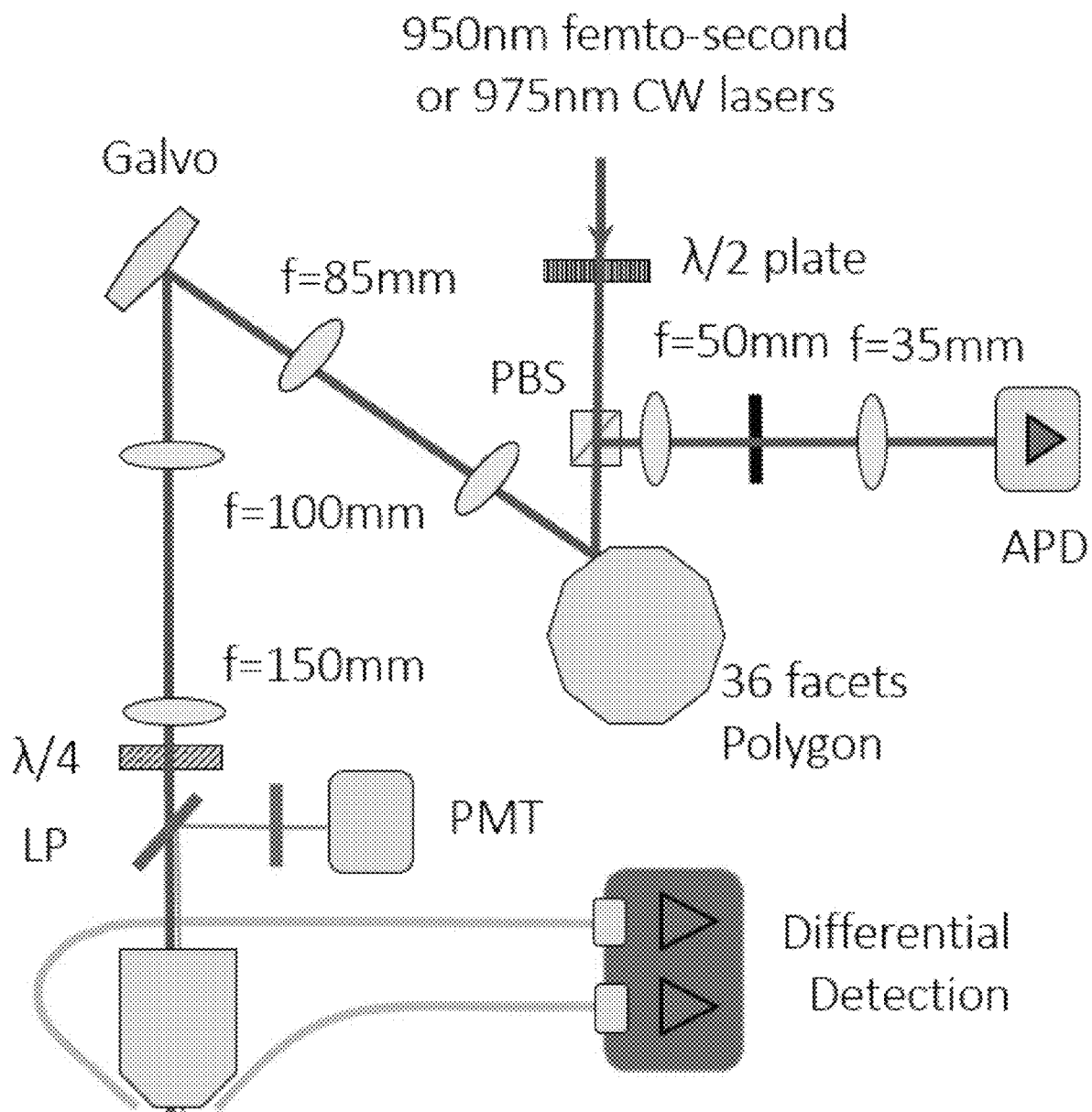
FIG. 14 shows an example of a system for in vivo flow cytometry using signals generated via differential epi-detection of forward scattered light in accordance with some embodiments of the disclosed subject matter.

FIG. 14 shows an example of a system for in vivo flow cytometry using signals generated via differential epi-detection of forward scattered light in accordance with some embodiments of the disclosed subject matter. The system represented in FIG. 14 combines a scanning OBM system, a confocal imaging arm, and a two photon fluorescence microscopy system that can be used simultaneously. The system represented in FIG. 14 was used to verify the viability of in vivo flow cytometer using signals generated via differential epi-detection of forward scattered light by recording blood flow in blood vessels of mouse ear skin. For comparison and verification, reflection confocal imaging system and two-photon imaging system were used to generate images of the same samples. The system represented in FIG. 14 includes a 36 facet polygon scanner (a Lincoln DT-36-275-040/SB12 from Cambridge Technology of Bedford, Mass.) that was used for fast axis scanning, and a galvanometer mirror (a model 6240 galvanometer scanner from Cambridge Technology) that was used for slow axis scanning. With this scanning configuration, rates of 33 thousand lines per second and up to 120 frames per second are achievable. The field of view of the microscope was 400 µm in normal view and 200 µm in 2× zoom view. The flow cytometer had two laser sources: a 50 mW, 975 nm continuous wave diode laser from Micro Laser System (model L49800M-240-TE) and a 50 mW femtosecond light source at 950 nm derived from a 1550 nm fiber laser (a CAZADERO laser available from Calmar Laser of Palo Alto, Calif.) with soliton self-frequency shifting and second harmonic conversion. A single mode 35 µm diameter photonic crystal fiber (available from NKT Photonics of Birkerød, Denmark) for 1900 nm soliton generation. A frequency doubling crystal (a BiBO crystal available from Newlight Photonics of North York, Canada) was used to generate 950 nm light.

The system represented in FIG. 14 included a differential epi-detection system that included two 1 mm core diameter multimode fibers (model M59L01 available from Thorlabs of Newton, N.J.), two avalanche photodiodes (model APD410A available from Thorlabs), and a custom differential and sum amplifier with high-pass filters at avalanche photodiode inputs and low-pass filters at amplifier outputs (similar to that shown in FIG. 12). Confocal reflectance light was detected using an avalanche photodiode (model APD410A available from Thorlabs). Two-photon fluorescence light was detected using a bandpass filter centered at 532 nm, a photomultiplier tube (model R7600U-200 available from Hamamatsu Photonics of Hamamatsu City, Japan) and a custom transimpedance amplifier. The sum and difference video signals, confocal reflectance video signals, and two-photon video signals were digitized and acquired using a 10-bit frame grabber (a Solios eAJXA Dual frame grabber available from Matrox Imaging of Dorval, Canada). Images were captured at 30 frames per second at full frame, 60 frames per second at half frame, and at 17 thousand lines per second in line scan mode. 5 mW laser power was applied at the sample.

The mice were anesthetized using isoflurane and placed on a 3-axis stage (a ROE200N stage available from Sutter Instrument of Novato Calif.) with a custom 3D printed mouse holder. A universal green fluorescent protein (GFP) mouse (beta-Actin GFP) was used to identify leukocytes for validation purposes.

The flow cytometer used two large-core-area multimode optical fibers attached to the two sides of objective for direct collection of forward scattered light in epi-collection mode. In some embodiments, near-infrared and visible light from each fiber can be split by a dichroic filter and detected by near-infrared and visible photodetectors. A high-speed analog signal processing and amplification system can be used to generate the real-time difference and sum signal for phase contrast and absorption contrast channels (e.g., as described above in connection with FIG. 13). For example, the difference signal can be generated from near-infrared photodetectors and the sum signal can be generated from visible photo detectors.

Figure 15:
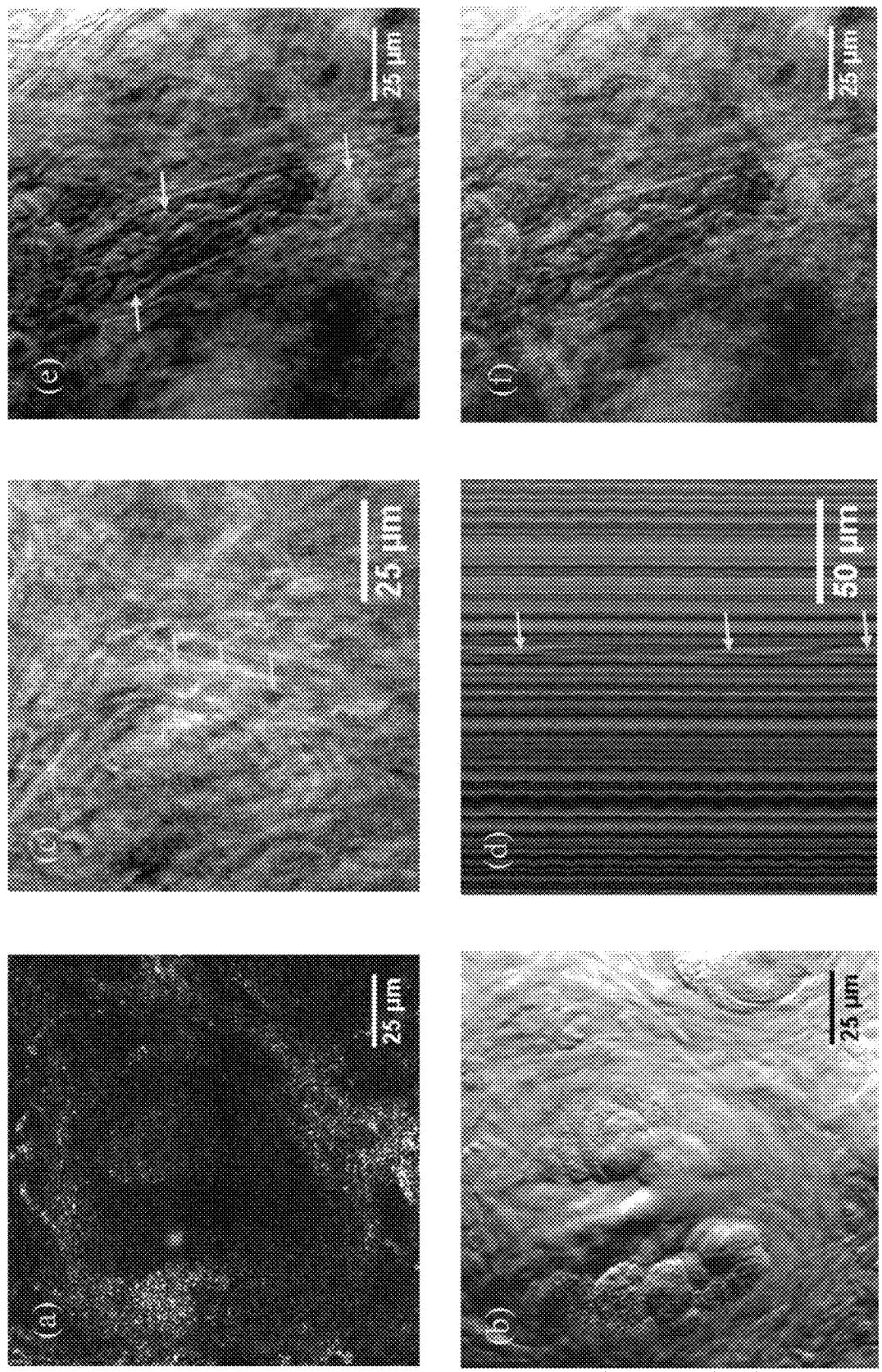
FIG. 15 shows examples of images of in vivo mouse ear skin generated using mechanisms described herein for differential epi-detection of forward scattered light, and corresponding images generated using confocal reflectance microscopy techniques.

FIG. 15 shows examples of images of in vivo mouse ear skin generated using mechanisms described herein for differential epi-detection of forward scattered light, and corresponding images generated using confocal reflectance microscopy techniques. FIG. 15 panels (a) and (b) are images of a hair follicle generated using the system represented in FIG. 14 using reflection confocal images (panel (a)) and differential epi-detection (panel (a)). The granular structure in the differential epi-detection image of panel (b) is a sebaceous gland in upper-mid dermis. As shown in FIG. 15, the differential epi-detection image has much higher contrast than the confocal reflectance image. The blood cells, endothelial cells and sebaceous gland are clearly visible in the differential epi-detection image.

FIG. 15 panels (b) and (c) show in vivo frame-scan and line-scan images of blood cells flowing in a capillary of mouse ear skin. The frame-scan image in panel (c) shows individual blood cells inside the capillary highlighted with arrows. Frame-scars data were taken at 30 frames per second. The line-scan image in panel (d) was taken at 17.2 thousand lines per second across a capillary. The blood cells were flowing at 2.3 mm/s through the capillary. These images confirm that differential epi-detection imaging techniques are capable of recording individual blood cells flowing in capillaries.

FIG. 15 panels (e) and (f) show in vivo frame-scan images of blood cells flowing in a relatively large blood vessel with GPF labeled leukocytes. Panel (e) shows a differential epi-detection image while panel (f) shows a composite image created from the differential epi-detection (gray) image and the two-photon (green) image.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (such as hard disks, floppy disks, etc.), optical media (such as compact discs, digital video discs, Blu-ray discs, etc.), semiconductor media (such as RAM, Flash memory, electrically programmable read only memory (EPROM), electrically erasable programmable read only memory (EEPROM), etc.), any suitable media that is not fleeting or devoid of any semblance of permanence during transmission, and/or any suitable tangible media. As another example, transitory computer readable media can include signals on networks, in wires, conductors, optical fibers, circuits, any other suitable media that is fleeting and devoid of any semblance of permanence during transmission, and/or any suitable intangible media.

It will be appreciated by those skilled in the art that while the disclosed subject matter has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is hereby incorporated by reference, as if each such patent or publication were individually incorporated by reference herein.

Various features and advantages of the invention are set forth in the following claims.

What is claimed is:

1. A system for differential phase contrast microscopy by transobjective differential epi-detection of forward scattered light, comprising:
  a scanning microscope comprising:
    a light source;
    an optical train defining an optical path of the scanning microscope having an optical axis comprising:
      scanning components optically coupled to the light source and configured to scan a beam from the light source across a surface of a sample; and
      a microscope objective optically coupled to the scanning components; and
  a detector mechanically coupled to the scanning microscope along the optical path within a first distance of a pupil plane of the optical train, the detector comprising:
    a printed circuit board defining a central aperture having a center configured to coincide with the optical axis of the optical path;
    a first photodiode mechanically coupled to the printed circuit board at a first radial distance from the center; and
    a second photodiode mechanically coupled to the printed circuit board at the first radial distance from the center and on an opposite side of the central aperture from the first photodiode, wherein the first distance is less than or equal to twice the first radial distance;
  an amplifier electrically coupled to the detector, comprising:
    a first transimpedance amplifier configured to receive a first current signal from the first photodiode and provide a first voltage signal;

a second transimpedance amplifier configured to receive a second current signal from the second photodiode and provide a second voltage signal;
a differential detection amplifier configured to receive the first voltage signal and the second voltage signal, and provide a third voltage signal indicative of a difference between the first voltage signal and the second voltage signal as an output; and
at least one hardware processor that is programmed to:
cause the light source to emit a beam of light toward the sample via the optical train;
cause the scanning components to scan the beam of light across the sample;
receive, from the differential detection amplifier, a plurality of output signals, each of the plurality of output signals indicative of a structure of the sample at a location at which the beam was focused;
generate an image based on the plurality of output signals; and
cause the image to be presented using a display.

2. The system of claim 1, wherein the detector is integrated within the microscope objective.

3. The system of claim 1, wherein the detector is mounted between the microscope objective and the second plurality of lenses, the detector further comprising:
a housing supporting the printed circuit board;
first threads configured to receive the microscope objective; and
second threads configured to mechanically couple the housing to the scanning microscope.

4. The system of claim 1, wherein the central aperture has a diameter of about 5 millimeters.

5. The system of claim 1, further comprising a confocal imaging system comprising:
a half wave plate having a first side optically coupled to the light source, and a second side;
a polarizing beam splitter having a first port optically coupled to the second side of the half wave plate, a second port optically coupled to a confocal imaging arm, and a third port optically coupled to the scanning components, and an interface that passes light having a first polarization and redirects light having a second polarization; and
a quarter wave plate having a first side optically coupled to the scanning components, and a second side optically coupled to the microscope objective;
wherein the hardware processor is further programmed to:
receive, from the confocal imaging arm, confocal reflectance imaging data indicative of a structure of the sample at locations at which the beam was focused; and
generate a second image based on the confocal reflectance imaging data in parallel with the image based on the plurality of output signals.

6. The system of claim 1, further comprising a plurality of lenses configured to optically generate a conjugate pupil plane within the optical path, wherein the detector is mounted within the first distance of the conjugate pupil plane.

7. The system of claim 1, wherein the scanning components comprise:
a first galvanometer optically coupled to the microscope objective; and
a polygon scanner or a second galvanometer, the polygon scanner or second galvanometer optically coupling the light source to the first galvanometer.

8. A microscope objective, comprising:
a housing having a first end and a second end, the second end comprising mounting threads;
a plurality of optical components defining an optical axis, the plurality of optical components comprising:
an objective lens mounted at the first end, the objective lens configured to collect light from a sample placed in a field of view of the objective lens,
wherein the plurality of optical components create a pupil plane at a first axial distance along the optical axis at which rays having the same angle of incidence on the objective lens from the within the field of view converge at the same radial distance from the optical axis;
a first photodetector mounted within the housing at a second axial distance along the optical axis and offset from the optical axis by a first radial distance; and
a second photodetector mounted within the housing at the second axial distance along the optical axis and offset from the optical axis by the first radial distance in a direction opposite from the first photodetector.

9. The microscope objective of claim 8, wherein the second axial distance is equal to the first axial distance.

10. The microscope objective of claim 8, further comprising a physical aperture collocated with the pupil plane, wherein the first photodetector and the second photodetector are mechanically coupled to the physical aperture.

11. The microscope objective of claim 8, further comprising a printed circuit board defining a central aperture having a center,
wherein the printed circuit board is mounted within the housing such that the center coincides with the optical axis, and
wherein the first photodetector and the second photodetector are mechanically coupled to printed circuit board, and electrically coupled to the first printed circuit board.

12. The microscope objective of claim 11, further comprising an amplifier electrically coupled to the printed circuit board, comprising:
a first transimpedance amplifier configured to receive a first current signal from the first photodiode and provide a first voltage signal;
a second transimpedance amplifier configured to receive a second current signal from the second photodiode and provide a second voltage signal;
a differential detection amplifier configured to receive the first voltage signal and the second voltage signal, and provide a third voltage signal indicative of a difference between the first voltage signal and the second voltage signal as an output.

13. The microscope objective of claim 11, wherein the printed circuit board acts as a physical aperture of the microscope objective and is collocated with the pupil plane.

14. The microscope objective of claim 11, wherein the first radial distance is in a range of 2 millimeters (mm) to 10 mm.

15. A detection apparatus for differential phase contrast microscopy by transobjective differential epi-detection of forward scattered light, comprising:
a housing configured to be mechanically coupled to a scanning microscope such that the housing is disposed along an optical path of the scanning microscope;
a substrate having a first surface and a second surface and an aperture defined by a through-hole from the first surface to the second surface, the substrate mounted within the housing such that, when the housing is mechanically coupled to the scanning microscope, the substrate is disposed along the optical path of the scanning microscope between an objective lens and an image plane associated with the objective lens;

a first photodetector mechanically coupled to the first surface of the substrate and disposed at a first distance from a side of the aperture; and a second photodetector mechanically coupled to the first surface of the substrate and disposed at the first distance from an opposite side of the aperture from the first photodetector, such that second photodetector is separated from the first photodetector by the diameter of the aperture and twice the first distance.

16. The detection apparatus of claim 15, wherein the housing is a microscope objective barrel.

17. The detection apparatus of claim 15, wherein the substrate comprises a printed circuit board, and wherein the first photodetector and the second photodetector are mechanically coupled to printed circuit board, and electrically coupled to the first printed circuit board.

18. The detection apparatus of claim 17, further comprising an amplifier electrically coupled to the printed circuit board, the amplifier comprising:

a first transimpedance amplifier configured to receive a first current signal from the first photodiode and provide a first voltage signal;

a second transimpedance amplifier configured to receive a second current signal from the second photodiode and provide a second voltage signal;

a differential detection amplifier configured to receive the first voltage signal and the second voltage signal, and provide a third voltage signal indicative of a difference between the first voltage signal and the second voltage signal as an output.

19. The detection apparatus of claim 17, wherein the first distance is in a range of 0.5 millimeters (mm) to 1 mm.

20. The detection apparatus of claim 15, further comprising:

a third photodetector mechanically coupled to the first surface of the substrate and disposed at the first distance from a perpendicular side of the aperture to the side along which the first photodetector is disposed; and a fourth photodetector mechanically coupled to the first surface of the substrate and disposed at the first distance from an opposite side of the aperture from the third photodetector.

21. A system for differential epi-detection of forward scattered light suitable for label free in vivo flow cytometry, comprising:

a scanning microscope comprising:

a first light source configured to emit light at a first wavelength;

a second light source configured to emit light at a second wavelength;

an optical train defining an optical path of the scanning microscope having an optical axis comprising:

scanning components optically coupled to the light source and configured to scan a beam from the light source across a surface of a sample; and a microscope objective optically coupled to the scanning optical components; and a detector arranged to receive light emitted by the first light source and the second light source that has been directed into a sample via the microscope objective, forward scattered through the sample, and re-emitted from the sample on the same side as the microscope objective, the detector comprising:

at least one pair of photodiodes optically coupled to detect forward scattered light emitted from the sample toward a first side of the microscope objective and a second side of the microscope objective that is opposite the first side;

an amplifier electrically coupled to the detector, comprising:

a differential amplifier configured to receive a first signal and a second signal from the at least one pair of photodiodes indicative of the intensity of light received at the first side of the microscope objective and the second side of the microscope objective at the first wavelength, respectively, and provide a signal indicative of a difference between the first signal and the second signal; and a sum amplifier configured to receive a third signal and a fourth signal from the at least one pair of photodiodes indicative of the intensity of light received at the first side of the microscope objective and the second side of the microscope objective at the second wavelength, respectively, and provide a signal indicative of a sum of the first signal and the second signal; and at least one hardware processor that is programmed to:

cause the first light source to emit a first beam of light toward a sample via the optical train;

cause the second light source to emit a second beam of light toward a sample via the optical train;

cause the scanning components to scan the first beam of light and the second beam of light across the sample;

receive, from the differential amplifier, a first plurality of output signals, each of the first plurality of output signals indicative of a structure of the sample at a location at which the first beam was focused;

receive, from the sum amplifier, a second plurality of output signals, each of the second plurality of output signals indicative of an absorption by the sample at a location at which the second beam was focused; and generate image data indicative of the presence of blood cells and leukocytes in the sample based on the first plurality of output signals and the second plurality of output signals.

22. The system of claim 21, wherein the detector is mechanically coupled to the scanning microscope along the optical path within a first distance of a pupil plane of the optical train, and the detector comprises:

a printed circuit board defining a central aperture having a center configured to coincide with the optical axis of the optical path; and the at least one pair of photodiodes comprises:

a first pair of photodiodes configured to inhibit detection of light of the second wavelength, the first pair of photodiodes comprising:

a first photodiode mechanically coupled to the printed circuit board at a first radial distance from the center;

a second photodiode mechanically coupled to the printed circuit board at the first radial distance from the center and on an opposite side of the central aperture from the first photodiode, wherein the first distance is less than or equal to twice the first radial distance; and a second pair of photodiodes configured to inhibit detection of light of the first wavelength, the second pair of photodiodes comprising:
- a third photodiode mechanically coupled to the printed circuit board at the first radial distance from the center;
- a fourth photodiode mechanically coupled to the printed circuit board at the first radial distance from the center and on an opposite side of the central aperture from the third photodiode.

23. The system of claim 21, wherein the first wavelength is in a range including near infrared light and excluding visible light, and the second wavelength is in a range including visible light and excluding near infrared light.

* * * * *

UNITED STATES PATENT AND TRADEMARK OFFICE
CERTIFICATE OF CORRECTION

PATENT NO. : 11,690,540 B2
APPLICATION NO. : 16/773438
DATED : July 4, 2023
INVENTOR(S) : Charles P. Lin et al.

It is certified that error appears in the above-identified patent and that said Letters Patent is hereby corrected as shown below:

In the Specification

Column 6, Line 34, "OF DRAWINGS" should be --OF THE DRAWINGS--.

Column 8, Line 44, "hack" should be --back--.

Column 8, Line 55, "he" should be --be--.

Column 22, Line 39, "nun" should be --mm--.

Column 25, Line 55, "Frame-scars" should be --Frame-scan--.

Signed and Sealed this
Nineteenth Day of September, 2023

Katherine Kelly Vidal
*Director of the United States Patent and Trademark Office*